(12) United States Patent
Palanivel et al.

(10) Patent No.: US 11,894,145 B2
(45) Date of Patent: Feb. 6, 2024

(54) DASHBOARD FOR TRACKING HEALTHY BUILDING PERFORMANCE

(71) Applicant: Honeywell International Inc., Charlotte, NC (US)

(72) Inventors: Rajkumar Palanivel, Eden Prairie, MN (US); Himanshu Khurana, Excelsior, MN (US); Deenadayalan Karunakaran, Bangalore (IN); Chandrakantha Chandra, Charlotte, NC (US); Hemant Jagannath Wadnere, Pune (IN); Ganapati Hegde, Charlotte, NC (US); Naveen Kumar Dindukurthi Sivaprasad, Bangalore (IN); Chen Xu, Shanghai (CN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 395 days.

(21) Appl. No.: 17/141,844

(22) Filed: Jan. 5, 2021

(65) Prior Publication Data
US 2022/0102007 A1 Mar. 31, 2022

Related U.S. Application Data

(60) Provisional application No. 63/085,921, filed on Sep. 30, 2020.

(51) Int. Cl.
G05B 15/02 (2006.01)
G16H 50/30 (2018.01)
(Continued)

(52) U.S. Cl.
CPC ............. *G16H 50/30* (2018.01); *F24F 11/63* (2018.01); *G05B 15/02* (2013.01); *G08B 21/02* (2013.01);
(Continued)

(58) Field of Classification Search
CPC ........ G16H 50/30; G16H 15/00; G16H 80/00; F24F 11/63; F24F 2110/10;
(Continued)

(56) References Cited

U.S. PATENT DOCUMENTS

| 191,512 A | 6/1877 | Bennett et al. |
| 4,009,647 A | 3/1977 | Howorth |

(Continued)

FOREIGN PATENT DOCUMENTS

| CA | 2387100 A1 | 11/2003 |
| CA | 2538139 A1 | 3/2005 |

(Continued)

OTHER PUBLICATIONS

Bocicor et al. "Wireless Sensor Network based System for the Prevention of Hospital Acquired Infections", arxiv.org, Cornell University Ithaca, NY 14853, May 2, 2017, XP080947042, (Abstract).

(Continued)

*Primary Examiner* — Michael W Choi
(74) *Attorney, Agent, or Firm* — Seager, Tufte & Wickhem, LLP

(57) ABSTRACT

A method of monitoring building compliance with healthy building guidelines includes obtaining current parameter values for a plurality of different parameters from a plurality of sensors disposed within a plurality of different zones of a building. For each of the parameters, the current parameter value received from each of the plurality of different zones is compared with a corresponding healthy building range for that parameter as specified by the healthy building guidelines. A healthy building dashboard is displayed that includes a summary that shows, for each of the plurality of different parameters, how many zones of the plurality of different zones of the building are within the corresponding healthy building range for that parameter and/or how many (Continued)

zones of the plurality of different zones are not within the corresponding healthy building range for that parameter.

17 Claims, 21 Drawing Sheets

(51) Int. Cl.
| | |
|---|---|
| *F24F 11/63* | (2018.01) |
| *G16H 15/00* | (2018.01) |
| *G16H 80/00* | (2018.01) |
| *G08B 21/02* | (2006.01) |
| *F24F 110/20* | (2018.01) |
| *F24F 110/70* | (2018.01) |
| *F24F 110/72* | (2018.01) |
| *F24F 110/10* | (2018.01) |

(52) U.S. Cl.
CPC ............. *G16H 15/00* (2018.01); *G16H 80/00* (2018.01); *F24F 2110/10* (2018.01); *F24F 2110/20* (2018.01); *F24F 2110/70* (2018.01); *F24F 2110/72* (2018.01)

(58) Field of Classification Search
CPC ............... F24F 2110/20; F24F 2110/70; F24F 2110/72; F24F 2120/10; G05B 15/02; G05B 19/048; G08B 21/02
See application file for complete search history.

(56) References Cited

U.S. PATENT DOCUMENTS

| | | |
|---|---|---|
| 4,375,637 A | 3/1983 | Desjardins |
| 4,918,615 A | 4/1990 | Suzuki et al. |
| 4,939,922 A | 7/1990 | Smalley et al. |
| 5,566,084 A | 10/1996 | Cmar |
| 5,727,579 A | 3/1998 | Chardack |
| 5,745,126 A | 4/1998 | Jain et al. |
| 5,751,916 A | 5/1998 | Kon et al. |
| 5,777,598 A | 7/1998 | Gowda et al. |
| 5,973,662 A | 10/1999 | Singers et al. |
| 6,065,842 A | 5/2000 | Fink |
| 6,139,177 A | 10/2000 | Venkatraman et al. |
| 6,144,993 A | 11/2000 | Fukunaga et al. |
| 6,157,943 A | 12/2000 | Meyer |
| 6,229,429 B1 | 5/2001 | Horon |
| 6,238,337 B1 | 5/2001 | Kambhatla et al. |
| 6,334,211 B1 | 12/2001 | Kojima et al. |
| 6,353,853 B1 | 3/2002 | Gravlin |
| 6,369,695 B2 | 4/2002 | Horon |
| 6,375,038 B1 | 4/2002 | Daansen et al. |
| 6,429,868 B1 | 8/2002 | Dehner, Jr. et al. |
| 6,473,084 B1 | 10/2002 | Phillips et al. |
| 6,487,457 B1 | 11/2002 | Hull et al. |
| 6,580,950 B1 | 6/2003 | Johnson et al. |
| 6,598,056 B1 | 7/2003 | Hull et al. |
| 6,619,555 B2 | 9/2003 | Rosen |
| 6,704,012 B1 | 3/2004 | Lefave |
| 6,720,874 B2 | 4/2004 | Fufido et al. |
| 6,741,915 B2 | 5/2004 | Poth |
| 6,796,896 B2 | 9/2004 | Laiti |
| 6,801,199 B1 | 10/2004 | Wallman |
| 6,816,878 B1 | 11/2004 | Zimmers et al. |
| 6,876,951 B2 | 4/2005 | Skidmore et al. |
| 6,882,278 B2 | 4/2005 | Winings et al. |
| 6,904,385 B1 | 6/2005 | Budike, Jr. |
| 6,907,387 B1 | 6/2005 | Reardon |
| 6,911,177 B2 | 6/2005 | Deal |
| 6,993,403 B1 | 1/2006 | Dadebo et al. |
| 6,993,417 B2 | 1/2006 | Osann, Jr. |
| 7,023,440 B1 | 4/2006 | Havekost et al. |
| 7,031,880 B1 | 4/2006 | Seem et al. |
| 7,062,722 B1 | 6/2006 | Carlin et al. |
| 7,110,843 B2 | 9/2006 | Pagnano et al. |
| 7,139,685 B2 | 11/2006 | Bascle et al. |
| 7,164,972 B2 | 1/2007 | Imhof et al. |
| 7,183,899 B2 | 2/2007 | Behnke |
| 7,200,639 B1 | 4/2007 | Yoshida |
| 7,222,111 B1 | 5/2007 | Budike, Jr. |
| 7,222,800 B2 | 5/2007 | Wruck |
| 7,257,397 B2 | 8/2007 | Shamoon et al. |
| D552,116 S | 10/2007 | Kurian et al. |
| 7,280,030 B1 | 10/2007 | Monaco |
| 7,292,908 B2 | 11/2007 | Borne et al. |
| 7,295,116 B2 | 11/2007 | Kumar et al. |
| 7,302,313 B2 | 11/2007 | Sharp et al. |
| 7,308,323 B2 | 12/2007 | Kruk et al. |
| 7,308,388 B2 | 12/2007 | Beverina et al. |
| 7,313,447 B2 | 12/2007 | Hsiung et al. |
| 7,346,433 B2 | 3/2008 | Budike, Jr. |
| 7,356,548 B1 | 4/2008 | Culp et al. |
| 7,379,782 B1 | 5/2008 | Cocco |
| 7,383,148 B2 | 6/2008 | Ahmed |
| 7,434,742 B2 | 10/2008 | Mueller et al. |
| 7,447,333 B1 | 11/2008 | Masticola et al. |
| 7,466,224 B2 | 12/2008 | Ward et al. |
| 7,496,472 B2 | 2/2009 | Seem |
| 7,512,450 B2 | 3/2009 | Ahmed |
| 7,516,490 B2 | 4/2009 | Riordan et al. |
| 7,548,833 B2 | 6/2009 | Ahmed |
| 7,551,092 B1 | 6/2009 | Henry |
| 7,557,729 B2 | 7/2009 | Hubbard et al. |
| 7,567,844 B2 | 7/2009 | Thomas et al. |
| 7,596,473 B2 | 9/2009 | Hansen et al. |
| 7,610,910 B2 | 11/2009 | Ahmed |
| 7,626,507 B2 | 12/2009 | LaCasse |
| 7,664,574 B2 | 2/2010 | Imhof et al. |
| 7,682,464 B2 | 3/2010 | Glenn et al. |
| 7,702,421 B2 | 4/2010 | Sullivan et al. |
| 7,729,882 B2 | 6/2010 | Seem |
| 7,755,494 B2 | 7/2010 | Melker et al. |
| 7,761,310 B2 | 7/2010 | Rodgers |
| 7,774,227 B2 | 8/2010 | Srivastava |
| 7,797,188 B2 | 9/2010 | Srivastava |
| 7,819,136 B1 | 10/2010 | Eddy |
| 7,822,806 B2 | 10/2010 | Frank et al. |
| 7,856,370 B2 | 12/2010 | Katta et al. |
| D640,264 S | 6/2011 | Fujii et al. |
| 7,978,083 B2 | 7/2011 | Melker et al. |
| 7,984,384 B2 | 7/2011 | Chaudhri et al. |
| 7,986,323 B2 | 7/2011 | Kobayashi et al. |
| 8,024,666 B2 | 9/2011 | Thompson |
| 8,086,047 B2 | 12/2011 | Penke et al. |
| 8,099,178 B2 | 1/2012 | Mairs et al. |
| 8,151,280 B2 | 4/2012 | Sather et al. |
| 8,176,095 B2 | 5/2012 | Murray et al. |
| 8,218,871 B2 | 7/2012 | Angell et al. |
| 8,219,660 B2 | 7/2012 | McCoy et al. |
| 8,271,941 B2 | 9/2012 | Zhang et al. |
| 8,294,585 B2 | 10/2012 | Barnhill |
| 8,302,020 B2 | 10/2012 | Louch et al. |
| 8,320,634 B2 | 11/2012 | Deutsch |
| 8,334,422 B2 | 12/2012 | Gutsol et al. |
| 8,344,893 B1 | 1/2013 | Drammeh |
| 8,375,118 B2 | 2/2013 | Hao et al. |
| 8,473,080 B2 | 6/2013 | Seem et al. |
| 8,476,590 B2 | 7/2013 | Stratmann et al. |
| 8,516,016 B2 | 8/2013 | Park et al. |
| 8,558,660 B2 | 10/2013 | Nix et al. |
| 8,639,527 B2 | 1/2014 | Rensvold et al. |
| 8,698,637 B2 | 4/2014 | Raichman |
| 8,816,860 B2 | 8/2014 | Ophardt et al. |
| 8,869,027 B2 | 10/2014 | Louch et al. |
| 8,904,497 B2 | 12/2014 | Hsieh |
| 8,936,944 B2 | 1/2015 | Peltz et al. |
| 8,947,437 B2 | 2/2015 | Garr et al. |
| 8,950,019 B2 | 2/2015 | Loberger et al. |
| 9,000,926 B2 | 4/2015 | Hollock et al. |
| 9,002,532 B2 | 4/2015 | Asmus |
| 9,030,325 B2 | 5/2015 | Taneff |
| 9,098,738 B2 | 8/2015 | Bilet et al. |
| 9,105,071 B2 | 8/2015 | Fletcher et al. |
| 9,175,356 B2 | 11/2015 | Peltz et al. |

(56) References Cited

U.S. PATENT DOCUMENTS

| | | |
|---|---|---|
| 9,235,657 B1 | 1/2016 | Wenzel et al. |
| 9,240,111 B2 | 1/2016 | Scott et al. |
| 9,256,702 B2 | 2/2016 | Elbsat et al. |
| 9,280,884 B1 | 3/2016 | Schultz et al. |
| 9,292,972 B2 | 3/2016 | Hailemariam et al. |
| 9,320,662 B2 | 4/2016 | Hayes et al. |
| 9,322,566 B2 | 4/2016 | Wenzel et al. |
| 9,355,069 B2 | 5/2016 | Tbsat et al. |
| D760,237 S | 6/2016 | Sabadosh et al. |
| 9,370,600 B1 | 6/2016 | DuPuis et al. |
| 9,373,242 B1 | 6/2016 | Conrad et al. |
| 9,396,638 B2 | 7/2016 | Wildman et al. |
| 9,311,807 B2 | 8/2016 | Schultz et al. |
| 9,406,212 B2 | 8/2016 | De Luca et al. |
| 9,418,535 B1 | 8/2016 | Felch et al. |
| 9,418,536 B1 | 8/2016 | Felch et al. |
| 9,436,179 B1 | 9/2016 | Turney et al. |
| 9,447,985 B2 | 9/2016 | Johnson, Jr. |
| 9,449,219 B2 | 9/2016 | Bilet et al. |
| 9,477,543 B2 | 10/2016 | Henley et al. |
| 9,497,832 B2 | 11/2016 | Verberkt et al. |
| D774,060 S | 12/2016 | Dias et al. |
| 9,513,364 B2 | 12/2016 | Hall et al. |
| 9,526,380 B2 | 12/2016 | Hamilton et al. |
| 9,526,806 B2 | 12/2016 | Park et al. |
| D776,693 S | 1/2017 | Linares et al. |
| 9,536,415 B2 | 1/2017 | De Luca et al. |
| 9,558,648 B2 | 1/2017 | Douglas |
| 9,568,204 B2 | 2/2017 | Asmus et al. |
| 9,581,985 B2 | 2/2017 | Walser et al. |
| 9,591,267 B2 | 3/2017 | Tipton et al. |
| 9,606,520 B2 | 3/2017 | Noboa et al. |
| 9,612,601 B2 | 4/2017 | Beyhaghi et al. |
| 9,613,518 B2 | 4/2017 | Dunn et al. |
| 9,618,224 B2 | 4/2017 | Emmons et al. |
| 9,640,059 B2 | 5/2017 | Hyland |
| 9,672,360 B2 | 6/2017 | Barkan |
| 9,696,054 B2 | 7/2017 | Asmus |
| 9,710,700 B2 | 7/2017 | Bilet et al. |
| 9,715,242 B2 | 7/2017 | Pillai et al. |
| 9,721,452 B2 | 8/2017 | Felch et al. |
| 9,729,945 B2 | 8/2017 | Schultz et al. |
| 9,778,639 B2 | 10/2017 | Boettcher et al. |
| 9,784,464 B2 | 10/2017 | Yamamoto et al. |
| 9,798,336 B2 | 10/2017 | Przybylski |
| 9,843,743 B2 | 12/2017 | Lewis et al. |
| 9,852,481 B1 | 12/2017 | Turney et al. |
| 9,856,634 B2 | 1/2018 | Rodenbeck et al. |
| 9,872,088 B2 | 1/2018 | Fadell et al. |
| 9,875,639 B2 | 1/2018 | Bone et al. |
| 9,911,312 B2 | 3/2018 | Wildman et al. |
| 9,940,819 B2 | 4/2018 | Ferniany |
| D818,474 S | 5/2018 | Kato et al. |
| 9,956,306 B2 | 5/2018 | Brais et al. |
| 9,982,903 B1 | 5/2018 | Ridder et al. |
| 9,986,175 B2 | 5/2018 | Frank et al. |
| 10,007,259 B2 | 6/2018 | Turney et al. |
| 10,055,114 B2 | 8/2018 | Shah et al. |
| 10,087,608 B2 | 10/2018 | Dobizl et al. |
| 10,101,730 B2 | 10/2018 | Wenzel et al. |
| 10,101,731 B2 | 10/2018 | Asmus et al. |
| 10,175,681 B2 | 1/2019 | Wenzel et al. |
| 10,222,083 B2 | 3/2019 | Drees et al. |
| 10,223,894 B2 | 3/2019 | Raichman |
| 10,228,837 B2 | 3/2019 | Hua et al. |
| 10,235,865 B2 | 3/2019 | Thyroff |
| 10,251,610 B2 | 4/2019 | Parthasarathy et al. |
| 10,282,796 B2 | 5/2019 | Tbsat et al. |
| 10,288,306 B2 | 5/2019 | Ridder et al. |
| 10,303,843 B2 | 5/2019 | Bitran et al. |
| 10,317,864 B2 | 6/2019 | Boettcher et al. |
| 10,332,382 B2 | 6/2019 | Thyroff |
| 10,359,748 B2 | 7/2019 | Elbsat et al. |
| 10,386,820 B2 | 8/2019 | Wenzel et al. |
| 10,402,767 B2 | 9/2019 | Noboa et al. |
| 10,514,178 B2 | 12/2019 | Willmott et al. |
| 10,514,817 B2 | 12/2019 | Hua et al. |
| 10,520,210 B2 | 12/2019 | Park et al. |
| 10,544,955 B2 | 1/2020 | Przybylski |
| 10,558,178 B2 | 2/2020 | Willmott et al. |
| 10,559,180 B2 | 2/2020 | Pourmohammad et al. |
| 10,559,181 B2 | 2/2020 | Pourmohammad et al. |
| 10,565,844 B2 | 2/2020 | Pourmohammad et al. |
| 10,600,263 B2 | 3/2020 | Park et al. |
| 10,602,474 B2 | 3/2020 | Goldstein |
| 10,605,477 B2 | 3/2020 | Ridder |
| 10,607,147 B2 | 3/2020 | Raykov et al. |
| 10,619,882 B2 | 4/2020 | Chatterjee et al. |
| 10,627,124 B2 | 4/2020 | Walser et al. |
| 10,673,380 B2 | 6/2020 | Wenzel et al. |
| 10,678,227 B2 | 6/2020 | Przybylski et al. |
| 10,706,375 B2 | 7/2020 | Wenzel et al. |
| 10,726,711 B2 | 7/2020 | Subramanian et al. |
| 10,732,584 B2 | 8/2020 | Elbsat et al. |
| 10,767,885 B2 | 9/2020 | Przybylski et al. |
| 10,775,988 B2 | 9/2020 | Narain et al. |
| 10,796,554 B2 | 10/2020 | Vincent et al. |
| 10,809,682 B2 | 10/2020 | Patil et al. |
| 10,809,705 B2 | 10/2020 | Przybylski |
| 10,824,125 B2 | 11/2020 | Elbsat et al. |
| 10,854,194 B2 | 12/2020 | Park et al. |
| 10,871,298 B2 | 12/2020 | Ridder et al. |
| 10,871,756 B2 † | 12/2020 | Johnson |
| 10,876,754 B2 | 12/2020 | Wenzel et al. |
| 10,890,904 B2 | 1/2021 | Turney et al. |
| 10,900,686 B2 | 1/2021 | Willmott et al. |
| 10,901,446 B2 | 1/2021 | Nesler et al. |
| 10,908,578 B2 | 2/2021 | Johnson, Jr. et al. |
| 10,909,642 B2 | 2/2021 | Elbsat et al. |
| 10,915,094 B2 | 2/2021 | Wenzel et al. |
| 10,917,740 B1 | 2/2021 | Scott et al. |
| 10,921,768 B2 | 2/2021 | Johnson, Jr. et al. |
| 10,921,972 B2 | 2/2021 | Park et al. |
| 10,921,973 B2 | 2/2021 | Park et al. |
| 10,928,790 B2 | 2/2021 | Mueller et al. |
| 10,948,884 B2 | 3/2021 | Beaty et al. |
| 10,949,777 B2 | 3/2021 | Elbsat et al. |
| 10,955,800 B2 | 3/2021 | Burroughs et al. |
| 10,956,842 B2 | 3/2021 | Wenzel et al. |
| 10,962,945 B2 | 3/2021 | Park et al. |
| 10,969,135 B2 | 4/2021 | Willmott et al. |
| 11,002,457 B2 | 5/2021 | Turney et al. |
| 11,009,252 B2 | 5/2021 | Turney et al. |
| 11,010,846 B2 | 5/2021 | Elbsat et al. |
| 11,016,648 B2 | 5/2021 | Fala et al. |
| 11,016,998 B2 | 5/2021 | Park et al. |
| 11,022,947 B2 | 6/2021 | Elbsat et al. |
| 11,024,292 B2 | 6/2021 | Park et al. |
| 11,036,249 B2 | 6/2021 | Elbsat |
| 11,038,709 B2 | 6/2021 | Park et al. |
| 11,042,139 B2 | 6/2021 | Deshpande et al. |
| 11,042,924 B2 | 6/2021 | Asmus et al. |
| 11,061,424 B2 | 7/2021 | Elbsat et al. |
| 11,068,821 B2 | 7/2021 | Wenzel et al. |
| 11,070,389 B2 | 7/2021 | Schuster et al. |
| 11,073,976 B2 | 7/2021 | Park et al. |
| 11,080,289 B2 | 8/2021 | Park et al. |
| 11,080,426 B2 | 8/2021 | Park et al. |
| 11,086,276 B2 | 8/2021 | Wenzel et al. |
| 11,094,186 B2 | 8/2021 | Razak |
| 11,108,587 B2 | 8/2021 | Park et al. |
| 11,131,473 B2 | 8/2021 | Risbeck et al. |
| 11,113,295 B2 | 9/2021 | Park et al. |
| 11,119,458 B2 | 9/2021 | Asp et al. |
| 11,120,012 B2 | 9/2021 | Park et al. |
| 11,150,617 B2 | 10/2021 | Ploegert et al. |
| 11,151,983 B2 | 10/2021 | Park et al. |
| 11,156,978 B2 | 10/2021 | Johnson, Jr. et al. |
| 11,156,996 B2 | 10/2021 | Schuster et al. |
| 11,158,306 B2 | 10/2021 | Park et al. |
| 11,182,047 B2 | 11/2021 | Nayak et al. |
| 11,188,093 B2 | 11/2021 | Ko et al. |
| 11,195,401 B2 | 12/2021 | Pourmohammad |
| 11,217,087 B2 | 1/2022 | Pelski |

(56) References Cited

U.S. PATENT DOCUMENTS

| | | |
|---|---|---|
| 11,226,126 B2 | 1/2022 | Przybylski et al. |
| 11,243,523 B2 | 2/2022 | Llopis et al. |
| 11,268,715 B2 | 3/2022 | Park et al. |
| 11,268,996 B2 | 3/2022 | Vitullo et al. |
| 11,269,505 B2 | 3/2022 | Fala et al. |
| 11,272,011 B1 | 3/2022 | Laughton et al. |
| 11,272,316 B2 | 3/2022 | Scott et al. |
| 11,275,348 B2 | 3/2022 | Park et al. |
| 11,275,363 B2 | 3/2022 | Przybylski et al. |
| 11,281,169 B2 | 3/2022 | Chatterjee et al. |
| 11,288,754 B2 | 3/2022 | Elbsat et al. |
| 11,314,726 B2 | 4/2022 | Park et al. |
| 11,314,788 B2 | 4/2022 | Park et al. |
| 11,334,044 B2 | 5/2022 | Goyal |
| 11,353,834 B2 | 6/2022 | Mueller et al. |
| 11,356,292 B2 | 6/2022 | Ploegert et al. |
| 11,360,451 B2 | 6/2022 | Pancholi et al. |
| 11,361,123 B2 | 6/2022 | Ploegert et al. |
| 2002/0111698 A1 | 8/2002 | Graziano et al. |
| 2002/0130868 A1 | 9/2002 | Smith |
| 2003/0028269 A1 | 2/2003 | Spriggs et al. |
| 2003/0030637 A1 | 2/2003 | Grinstein et al. |
| 2003/0046862 A1 | 3/2003 | Wolf et al. |
| 2003/0071814 A1 | 4/2003 | Jou et al. |
| 2003/0078677 A1 | 4/2003 | Hull et al. |
| 2003/0083957 A1 | 5/2003 | Olefson |
| 2003/0103075 A1 | 6/2003 | Rosselot |
| 2003/0171851 A1 | 9/2003 | Brickfield et al. |
| 2003/0214400 A1 | 11/2003 | Mizutani et al. |
| 2003/0233432 A1 | 12/2003 | Davis et al. |
| 2004/0001009 A1 | 1/2004 | Winings et al. |
| 2004/0064260 A1 | 4/2004 | Padmanabhan et al. |
| 2004/0143474 A1 | 7/2004 | Haeberle et al. |
| 2004/0153437 A1 | 8/2004 | Buchan |
| 2004/0168115 A1 | 8/2004 | Bauernschmidt et al. |
| 2004/0233192 A1 | 11/2004 | Hopper |
| 2004/0260411 A1 | 12/2004 | Cannon |
| 2005/0010460 A1 | 1/2005 | Mizoguchi et al. |
| 2005/0119767 A1 | 6/2005 | Kiwimagi et al. |
| 2005/0143863 A1 | 6/2005 | Ruane et al. |
| 2005/0267900 A1 | 12/2005 | Ahmed et al. |
| 2006/0004841 A1 | 1/2006 | Heikkonen et al. |
| 2006/0009862 A1 | 1/2006 | Imhof et al. |
| 2006/0017547 A1 | 1/2006 | Buckingham et al. |
| 2006/0020177 A1 | 1/2006 | Seo et al. |
| 2006/0028471 A1 | 2/2006 | Kincaid et al. |
| 2006/0029256 A1 | 2/2006 | Miyoshi et al. |
| 2006/0058900 A1 | 3/2006 | Johanson et al. |
| 2006/0067545 A1 | 3/2006 | Ewis et al. |
| 2006/0067546 A1 | 3/2006 | Lewis et al. |
| 2006/0077255 A1 | 4/2006 | Cheng |
| 2006/0184326 A1 | 8/2006 | McNally et al. |
| 2006/0231568 A1 | 10/2006 | Lynn et al. |
| 2006/0265664 A1 | 11/2006 | Simons et al. |
| 2006/0279630 A1 | 12/2006 | Aggarwal et al. |
| 2007/0016955 A1 | 1/2007 | Goldberg et al. |
| 2007/0055757 A1 | 3/2007 | Mairs et al. |
| 2007/0055760 A1 | 3/2007 | McCoy et al. |
| 2007/0061046 A1 | 3/2007 | Mairs et al. |
| 2007/0067062 A1 | 3/2007 | Mairs et al. |
| 2007/0088534 A1 | 4/2007 | MacArthur et al. |
| 2007/0090951 A1 | 4/2007 | Chan et al. |
| 2007/0091091 A1 | 4/2007 | Gardiner et al. |
| 2007/0101433 A1 | 5/2007 | Louch et al. |
| 2007/0114295 A1 | 5/2007 | Jenkins |
| 2007/0120652 A1 | 5/2007 | Behnke |
| 2007/0139208 A1 | 6/2007 | Kates |
| 2007/0216682 A1 | 9/2007 | Navratil et al. |
| 2007/0219645 A1 | 9/2007 | Thomas et al. |
| 2007/0239484 A1 | 10/2007 | Arond et al. |
| 2007/0268122 A1 | 11/2007 | Kow et al. |
| 2008/0001763 A1 | 1/2008 | Raja et al. |
| 2008/0027885 A1 | 1/2008 | Van Putten et al. |
| 2008/0036593 A1 | 2/2008 | Rose-Pehrsson et al. |
| 2008/0046388 A1 | 2/2008 | Budike, Jr. |
| 2008/0062167 A1 | 3/2008 | Boggs et al. |
| 2008/0099045 A1 | 5/2008 | Glenn et al. |
| 2008/0103798 A1 | 5/2008 | Domenikos et al. |
| 2008/0120396 A1 | 5/2008 | Jayaram et al. |
| 2008/0144885 A1 | 6/2008 | Zucherman et al. |
| 2008/0183424 A1 | 7/2008 | Seem |
| 2008/0194009 A1 | 8/2008 | Marentis |
| 2008/0198231 A1 | 8/2008 | Ozdemir et al. |
| 2008/0209342 A1 | 8/2008 | Taylor et al. |
| 2008/0222565 A1 | 9/2008 | Taylor et al. |
| 2008/0224862 A1 | 9/2008 | Cirker |
| 2008/0242945 A1 | 10/2008 | Gugliotti et al. |
| 2008/0250800 A1 | 10/2008 | Wetzel |
| 2008/0279420 A1 | 11/2008 | Masticola et al. |
| 2008/0280275 A1 | 11/2008 | Collopy |
| 2008/0303658 A1 | 12/2008 | Melker et al. |
| 2008/0306985 A1 | 12/2008 | Murray et al. |
| 2008/0320552 A1 | 12/2008 | Kumar et al. |
| 2009/0001181 A1 | 1/2009 | Siddaramanna et al. |
| 2009/0024944 A1 | 1/2009 | Louch et al. |
| 2009/0065596 A1 | 3/2009 | Seem et al. |
| 2009/0083120 A1 | 3/2009 | Strichman et al. |
| 2009/0096791 A1 | 4/2009 | Abshear et al. |
| 2009/0125337 A1 | 5/2009 | Abri |
| 2009/0125825 A1 | 5/2009 | Rye et al. |
| 2009/0144023 A1 | 6/2009 | Seem |
| 2009/0157744 A1 | 6/2009 | McConnell |
| 2009/0160673 A1 | 6/2009 | Cirker |
| 2009/0322782 A1 | 12/2009 | Kimchi et al. |
| 2010/0048167 A1 | 2/2010 | Chow et al. |
| 2010/0058248 A1 | 3/2010 | Park |
| 2010/0064001 A1 | 3/2010 | Daily |
| 2010/0070089 A1 | 3/2010 | Harrod et al. |
| 2010/0073162 A1 | 3/2010 | Johnson et al. |
| 2010/0106308 A1* | 4/2010 | Filbeck ............... G05B 15/02 700/276 |
| 2010/0123560 A1 | 5/2010 | Nix et al. |
| 2010/0134296 A1 | 6/2010 | Hwang |
| 2010/0156628 A1 | 6/2010 | Ainsbury et al. |
| 2010/0156630 A1 | 6/2010 | Ainsbury |
| 2010/0188228 A1 | 7/2010 | Hyland |
| 2010/0223198 A1 | 9/2010 | Noureldin et al. |
| 2010/0249955 A1 | 9/2010 | Sitton |
| 2010/0286937 A1 | 11/2010 | Hedley et al. |
| 2010/0318200 A1 | 12/2010 | Foslien et al. |
| 2010/0324962 A1 | 12/2010 | Nesler et al. |
| 2011/0010654 A1 | 1/2011 | Raymond et al. |
| 2011/0057799 A1 | 3/2011 | Taneff |
| 2011/0077779 A1 | 3/2011 | Fuller et al. |
| 2011/0083094 A1 | 4/2011 | Laycock et al. |
| 2011/0087988 A1 | 4/2011 | Ray et al. |
| 2011/0112854 A1 | 5/2011 | Koch et al. |
| 2011/0126111 A1 | 5/2011 | Gill et al. |
| 2011/0154426 A1 | 6/2011 | Doser et al. |
| 2011/0161124 A1* | 6/2011 | Lappinga ............. G06Q 10/063 705/314 |
| 2011/0169646 A1 | 7/2011 | Raichman |
| 2011/0184563 A1 | 7/2011 | Foslien et al. |
| 2011/0202467 A1 | 8/2011 | Hilber et al. |
| 2011/0273298 A1 | 11/2011 | Snodgrass et al. |
| 2011/0291841 A1 | 12/2011 | Hollock et al. |
| 2011/0298301 A1 | 12/2011 | Wong et al. |
| 2011/0316703 A1 | 12/2011 | Butler et al. |
| 2011/0320054 A1 | 12/2011 | Brzezowski |
| 2012/0022700 A1 | 1/2012 | Drees et al. |
| 2012/0039503 A1 | 2/2012 | Chen et al. |
| 2012/0062382 A1 | 3/2012 | Taneff |
| 2012/0075464 A1 | 3/2012 | Derenne et al. |
| 2012/0109988 A1 | 5/2012 | Li et al. |
| 2012/0112883 A1 | 5/2012 | Wallace et al. |
| 2012/0131217 A1 | 5/2012 | Delorme et al. |
| 2012/0158185 A1 | 6/2012 | El-Mankabady et al. |
| 2012/0216243 A1 | 8/2012 | Gill et al. |
| 2012/0224057 A1 | 9/2012 | Gill et al. |
| 2012/0259466 A1 | 10/2012 | Ray et al. |
| 2012/0262472 A1 | 10/2012 | Garr et al. |
| 2012/0272146 A1 | 10/2012 | D'souza et al. |
| 2012/0291068 A1 | 11/2012 | Khushoo et al. |
| 2012/0303652 A1 | 11/2012 | Tseng |

(56) References Cited

U.S. PATENT DOCUMENTS

| | | |
|---|---|---|
| 2012/0310418 A1 | 12/2012 | Harrod et al. |
| 2013/0055132 A1 | 2/2013 | Foslien |
| 2013/0060794 A1 | 3/2013 | Puttabasappa et al. |
| 2013/0082842 A1 | 4/2013 | Balazs et al. |
| 2013/0086152 A1 | 4/2013 | Hersche et al. |
| 2013/0091631 A1 | 4/2013 | Tayes et al. |
| 2013/0110295 A1 | 5/2013 | Zheng et al. |
| 2013/0169681 A1 | 7/2013 | Rasane et al. |
| 2013/0184880 A1 | 7/2013 | McMahon |
| 2013/0187775 A1 | 7/2013 | Marsden et al. |
| 2013/0204570 A1 | 8/2013 | Mendelson et al. |
| 2013/0229276 A1 | 9/2013 | Hunter |
| 2013/0268293 A1 | 10/2013 | Knudson et al. |
| 2013/0289774 A1 | 10/2013 | Day et al. |
| 2013/0338837 A1 | 12/2013 | Hublou et al. |
| 2014/0032157 A1 | 1/2014 | Khiani |
| 2014/0040998 A1 | 2/2014 | Hsieh |
| 2014/0046490 A1 | 2/2014 | Foslien et al. |
| 2014/0046722 A1 | 2/2014 | Rosenbloom et al. |
| 2014/0058539 A1 | 2/2014 | Park |
| 2014/0167917 A2 | 6/2014 | Wallace et al. |
| 2014/0207291 A1 | 7/2014 | Golden et al. |
| 2014/0292518 A1 | 10/2014 | Wildman et al. |
| 2014/0307076 A1 | 10/2014 | Deutsch |
| 2014/0309757 A1 | 10/2014 | Le Sant et al. |
| 2014/0316582 A1 | 10/2014 | Berg-Sonne et al. |
| 2014/0320289 A1 | 10/2014 | Raichman |
| 2014/0342724 A1 | 11/2014 | Hill et al. |
| 2015/0025329 A1 | 1/2015 | Amarasingham et al. |
| 2015/0032264 A1 | 1/2015 | Emmons et al. |
| 2015/0056909 A1 | 2/2015 | Chien |
| 2015/0070174 A1 | 3/2015 | Douglas |
| 2015/0077258 A1 | 3/2015 | Nelson et al. |
| 2015/0113462 A1 | 4/2015 | Chen et al. |
| 2015/0153918 A1 | 6/2015 | Chen et al. |
| 2015/0161874 A1 | 6/2015 | Thyroff et al. |
| 2015/0167995 A1 | 6/2015 | Fadell et al. |
| 2015/0168949 A1 | 6/2015 | Hua et al. |
| 2015/0194043 A1 | 7/2015 | Dunn et al. |
| 2015/0198707 A1 | 7/2015 | Al-Alusi |
| 2015/0212717 A1 | 7/2015 | Nair et al. |
| 2015/0213222 A1 | 7/2015 | Amarasingham et al. |
| 2015/0213379 A1 | 7/2015 | Nair et al. |
| 2015/0216369 A1 | 8/2015 | Hamilton et al. |
| 2015/0253748 A1 | 9/2015 | Brun et al. |
| 2015/0281287 A1 | 10/2015 | Gill et al. |
| 2016/0061473 A1 | 3/2016 | Johnson, Jr. |
| 2016/0061476 A1 | 3/2016 | Schultz et al. |
| 2016/0061477 A1 | 3/2016 | Schultz et al. |
| 2016/0061794 A1 | 3/2016 | Schultz et al. |
| 2016/0061795 A1 | 3/2016 | Schultz et al. |
| 2016/0063833 A1 | 3/2016 | Schultz et al. |
| 2016/0066067 A1 | 3/2016 | Schultz et al. |
| 2016/0116181 A1 | 4/2016 | Aultman et al. |
| 2016/0139067 A1 | 5/2016 | Grace |
| 2016/0253897 A1 | 9/2016 | Wildman et al. |
| 2016/0255516 A1 | 9/2016 | Hill et al. |
| 2016/0298864 A1 | 10/2016 | Ekolind et al. |
| 2016/0306934 A1 | 10/2016 | Sperry et al. |
| 2016/0314683 A1 | 10/2016 | Felch et al. |
| 2016/0328948 A1 | 11/2016 | Ferniany |
| 2016/0335731 A1 | 11/2016 | Hall |
| 2016/0367925 A1 | 12/2016 | Blackley |
| 2017/0024986 A1 | 1/2017 | Austin |
| 2017/0193792 A1 | 7/2017 | Bermudez Rodriguez et al. |
| 2017/0256155 A1 | 9/2017 | Sengstaken, Jr. |
| 2017/0280949 A1 | 10/2017 | Wildman et al. |
| 2017/0294106 A1 | 10/2017 | Thyroff |
| 2017/0365024 A1 | 12/2017 | Koch et al. |
| 2018/0016773 A1 | 1/2018 | Chandler et al. |
| 2018/0151054 A1 | 5/2018 | Pi |
| 2018/0218591 A1 | 8/2018 | Easter |
| 2018/0259927 A1 | 9/2018 | Przybylski et al. |
| 2018/0259934 A1 | 9/2018 | Piaskowski et al. |
| 2018/0293038 A1 | 10/2018 | Meruva et al. |
| 2018/0301014 A1 | 10/2018 | Worral et al. |
| 2018/0313695 A1 | 11/2018 | Shim et al. |
| 2018/0365957 A1 | 12/2018 | Wright et al. |
| 2019/0051138 A1 | 2/2019 | Easter |
| 2019/0122759 A1* | 4/2019 | Wakimoto ............. G16H 40/20 |
| 2019/0139395 A1 | 5/2019 | Rogachev et al. |
| 2019/0156443 A1 | 5/2019 | Hall |
| 2019/0209719 A1 | 7/2019 | Andersen et al. |
| 2020/0009280 A1 | 1/2020 | Kupa et al. |
| 2020/0074836 A1 | 3/2020 | Kolavennu et al. |
| 2020/0090089 A1 | 3/2020 | Aston et al. |
| 2020/0146557 A1 | 5/2020 | Cheung et al. |
| 2020/0200420 A1 | 6/2020 | Nayak et al. |
| 2020/0227159 A1 | 7/2020 | Boisvert et al. |
| 2020/0256571 A1 | 8/2020 | Johnson, Jr. et al. |
| 2021/0010701 A1 | 1/2021 | Suindykov et al. |
| 2021/0011443 A1 | 1/2021 | Mcnamara et al. |
| 2021/0011444 A1 | 1/2021 | Risbeck et al. |
| 2021/0041125 A1* | 2/2021 | Liu ......................... F24F 11/65 |
| 2021/0356927 A1 | 11/2021 | Johnson, Jr. et al. |
| 2021/0364181 A1 | 11/2021 | Risbeck et al. |
| 2021/0373519 A1 | 12/2021 | Risbeck et al. |
| 2022/0011731 A1 | 1/2022 | Risbeck et al. |
| 2022/0058556 A1* | 2/2022 | Warake ............ G05B 19/41845 |
| 2022/0113045 A1 | 4/2022 | Gamroth et al. |
| 2022/0137580 A1 | 5/2022 | Burroughs et al. |

FOREIGN PATENT DOCUMENTS

| | | |
|---|---|---|
| CN | 103110410 A | 5/2013 |
| CN | 103970977 A | 8/2014 |
| CN | 105116848 A | 12/2015 |
| CN | 108961714 A | 12/2018 |
| CN | 110009245 A | 7/2019 |
| CN | 110084928 A | 8/2019 |
| CN | 110827457 A | 2/2020 |
| EP | 1669912 A1 | 6/2006 |
| EP | 2310981 A1 | 4/2011 |
| JP | 7085166 A | 3/1995 |
| JP | 11024735 A | 1/1999 |
| JP | 11317936 A | 11/1999 |
| JP | 2001356813 A | 12/2001 |
| JP | 2005242531 A | 9/2005 |
| JP | 2005311563 A | 11/2005 |
| KR | 1172747 B1 | 8/2012 |
| KR | 101445367 B1 | 10/2014 |
| KR | 1499081 B1 | 3/2015 |
| WO | 9621264 A3 | 11/1996 |
| WO | 2004029518 A1 | 4/2004 |
| WO | 2005045715 A2 | 5/2005 |
| WO | 2008152433 A1 | 12/2008 |
| WO | 2008157755 A1 | 12/2008 |
| WO | 2009012319 A2 | 1/2009 |
| WO | 2009079648 A1 | 6/2009 |
| WO | 2010106474 A1 | 9/2010 |
| WO | 2011025085 A1 | 3/2011 |
| WO | 2011043732 A1 | 4/2011 |
| WO | 2011057173 A2 | 5/2011 |
| WO | 2011123743 A1 | 10/2011 |
| WO | 2013062725 A1 | 5/2013 |
| WO | 2013178819 A1 | 12/2013 |
| WO | 2014009291 A1 | 1/2014 |
| WO | 2014098861 A1 | 6/2014 |
| WO | 2014135517 A1 | 9/2014 |
| WO | 2016123536 A1 | 8/2016 |
| WO | 2017057274 A1 | 4/2017 |
| WO | 2019046580 A1 | 3/2019 |
| WO | 2020024553 A1 | 2/2020 |

OTHER PUBLICATIONS

Shhedi et al., "Traditional and ICT Solutions for Preventing the Hospital Acquired Infection", 2015 20th International Conference on Control Systems and Computer Science, IEEE, May 27, 2015, pp. 867-873, XP033188038.

Extended European Search Report, EP application No. 20151295.1, pp. 13, dated May 26, 2020.

U.S. Appl. No. 14/109,496, filed Dec. 17, 2013.

(56) References Cited

OTHER PUBLICATIONS

"What is the GE Nucleus Home Manager? How can a Home Manager Help with Energy Conservation?" GE Nucleus, 2 pages, printed Jan. 15, 2013. www.geappliances.com/home-energy-manager/about-energy-monitors.htm.
"Lucid Design Group—Building Dashboard Network—Apps," 7 pages, Jan. 15, 2013. www.luciddesigngroup.com/network/apps.php#homepage.
Preuveneers et al., "Intelligent Widgets for Intuitive Interaction and Coordination in Smart Home Environments," IEEE Eighth International Conference on Intelligent Environments, pp. 157-164, 2012.
Wu et al., "A Web 2.0 Based Scientific Application Framework," 7 pages, prior to Jul. 24, 2014.
"The Home Dashboard," CRBM info@hand website, 46 pages, prior to Apr. 25, 2013.
"Free Facilities Dashboards," eSight Energy Website, 2 pages, prior to Apr. 25, 2013.
Alerton Building Controls, Gallery Prints, 7 pages, Dec. 19, 2013.
Carter, "Industrial Energy Management Dashboards Require a Toolkit," Cross Automation, 11 pages, Nov. 4, 2013.
U.S. Appl. No. 14/169,071, filed Jan. 30, 2014.
U.S. Appl. No. 14/169,083, filed Jan. 30, 2014.
U.S. Appl. No. 14/461,188, filed Aug. 15, 2014.
U.S. Appl. No. 14/482,607, filed Sep. 10, 2014.
e-homecontrols.com, "e-Home Controls Website," link to actual website no longer works, 1 page, prior to Dec. 19, 2013.
"C&C (/)—Omniboard," 5 pages, Dec. 19, 2013. http://www.ccbac.com.
"DomController Home Automation Software—Control Anything from Anywhere," 11 pages, printed Jan. 6, 2015. http://www.domcontroller.com/en/.
"Novar OPUS BAS," 1 page, prior to Feb. 13, 2013. http://www.novar.com/ems-bas/opus-building-automation-system.
"A 3D Interactive Environment for Automated Building Control," Master's Dissertation, Instituto Superior Tecnico, 120 pages, Nov. 2012.
Panduit Corp., "Enable a Building Automation with Panduit Enterprise Solutions," 4 pages, Nov. 2012.
Honeywell, "WEBs-AX Web-Enabled Building Solutions," sales brochure, Honeywell International Inc., Mar. 2009.
Honeywell, "Attune Advisory Services," press release, Honeywell International Inc., Mar. 20, 2012.
EnteliWEB Overview, web pages retrieved on May 9, 2013 from http://deltacontrols.com/products/facilities-management/supervisory-software et seq. by the Internet Archive at web.archive.org.
"BACnet Protocol Implementation Conformance Statement" for enteliWEB, Delta Controls, Jul. 17, 2013.
Castle, "7 Software Platforms that Make Building Energy Management Easy," http://greentechadvocates.com/2012/11/28/7-software-platforms-that-make-building-energy-managment-easy/, Nov. 28, 2012.
EnteliWEB "Software: Enterprise Energy Management", catalog sheet, Delta Controls, 2012.
EnteliWEB "Software: Enterprise Energy Management", catalog sheet, Delta Controls., 2010.
"Intelligent Building Management Systems in Miami," Advanced Control Corp., Mar. 7, 2013.
"The Ohio State University," BACnet International Journal, vol. 5, p. 4, Jan. 2013.
Bobker et al., "Operational Effectiveness in Use of BAS," Proceedings of the 13th International Conference for Enhanced Building Operations, Oct. 8, 2013.
Castelo, "A 3D Interactive Environment for Automated Building Control," Elsevier, Nov. 8, 2012.
"Creston Special Report: How Intelligent building management solutions are reducing operational costs," Creston, 2012.
"Building Automation Software Solutions," Iconics, 2013.
Lacey, "The Top 10 Software Vendors Connecting Smart Buildings to the Smart Grid," http://www.greentechmedia.com/articles/read/the-top-10-companies-in-enterprise-smart-grid, Jul. 18, 2013.
"NiagraAX Product Model Overview," Tridium, Inc., 2005.
"An Overview of NiagraAX: A comprehensive software platform designed to create smart device applications," Tridium, Inc., 2005.
"Phoenix Controls Portal," Phoenix Controls, Inc., 2013.
Quirk, "A Brief History of BIM," Arch Daily, Dec. 7, 2012.
Samad et al., "Leveraging the Web: A Universal Framework for Building Automation," Proceedings of the 2007 American Control Conference, Jul. 11, 2007.
Sinha et al., "9 Key attributes of energy dashboards and analytics tools," Aug. 28, 2013, https://www.greenbiz.com/blog/2013/08/28/9-key-attributes-energy-dashboards-and=analytics-tools.
Sinopoli, "Dashboards For Buildings," http://www/automatedbuildings.com/news/dec10/articles/sinopoli/101119034404sinopoli.html, Dec. 2010.
Sinopoli, "Modeling Building Automation and Control Systems," http://www.automatedbuildings.com/news/jun13/articles/sinopoli/130521122303sinopoli.html, Jun. 2013.
Zito, "What is Tridium Part 1," http://blog.buildingautomationmonthly.com/what-is-tridium/, May 12, 2013.
Zito, "What is Tridium Part 2," http://blog.buildingautomationmonthly.com/tridium-part-2/, Sep. 10, 2013.
International Search Report and Written Opinion dated Jul. 17, 2018 for International PCT Application No. PCT/US2018/025189 (12 pages).
"Data analytics and smart buildings increase comfort and energy efficiency", https://www.microsoft.com/itshowcase/Article/Content/845/Data-analytics-and-smart-buildings-increase-comfort-and-energy-efficiency, Dec. 19, 2016, 8 pages.
Donnelly, "Building Energy Management: Using Data as a Tool", http://www.buildingefficiencyinitiative.org/sites/default/files/legacy/InstituteBE/media/Library/Resources/Existing-Building-Retrofits/Using-Building-Data-as-a-Tool.pdf, Oct. 2012, 9 pages.
"ASHRAE Dashboard Research Project," 29 pages, Aug. 28, 2008.
Honeywell, "Energy Manager User Guide," Release 3.2, 180 pages, 2008.
"Fuzzy Logic Toolbox 2.1, Design and Stimulate Fuzzy Logic Systems," The MathWorks, 2 pages, May 2004.
"Junk Charts, Recycling Chartjunk as junk art," 3 pages, Oct. 2, 2006.
"Model Predictive Control Toolbox 2, Develop Internal Model-Based Controllers for Constrained Multivariable Processes," The MathWorks, 4 pages, Mar. 2005.
Honeywell, "Product Guide 2004," XP-002472407, 127 pages, 2004.
"Statistics Toolbox, for Use with Matlab," User's Guide Version2, The MathWorks, 408 pages, Jan. 1999.
"Vykon Energy Suite Student Guide," Tridium Inc., 307 pages, Mar. 3, 2006.
"Web Based Energy Information Systems for Energy Management and Demand Response in Commercial Buildings," California Energy Commission, 80 pages, Oct. 2003.
Andover Controls, Network News, vol. 2, No. 2, 8 pages, 1997.
Andover Controls World, 4 pages, Spring 1997.
Bell et al., "Early Event Detection-Results from a Prototype Implementation," AICHE Spring National Meeting, 15 pages, Apr. 2005.
Cadgraphics, "The CADGRAPHICS User's Guide," 198 pages, 2003.
Carrier Comfort Network CCN Web, "Web Browser User Interface to the Carrier Comfort Network," 2 pages, 2002.
Carrier Comfort Network CCN Web, Overview and Configuration Manual, 134 pages, Apr. 2006.
Carrier Comfort Network CCN Web, Product Data, 2 pages, Apr. 2006.
Carrier, "i-Vu Powerful and Intuitive Front End for Building Control," 2 pages, Aug. 2005.
Carrier, "i-Vu Web-Based Integrated Control System," 3 pages, 2005.
Carrier, Demo Screen Shots, 15 pages, prior to Aug. 27, 2007.
Carrier, i-Vu CCN 4.0, Owner's Guide, 20 pages, Jul. 2007.
Carrier, i-Vu CCN, 7 pages, 2007.
Chan, "Rank Revealing QR Factorizations," Linear Algebra and It's Applications, vol. 88-89, p. 67-82, Apr. 1987.

(56) References Cited

OTHER PUBLICATIONS

Circon, "i-Browse Web-Based Monitoring and Control for Facility Management," 2 pages, prior to Aug. 27, 2007.
Australian Application 2009904740, Published copy, 28 pages, Application Filed on Sep. 29, 2009.
Echelon, "Energy Control Solutions with the i.Lon SmartServer," 4 pages, 2007.
Echelon, "i.Lon 100e3 Internet Server Models 72101R-300, 72101R-308, 72102R-300, 72103-R300 . . ." 5 pages, copyright 2002-2007.
Echelon, "i.Lon 100e3 Internet Server New Features," 15 pages, Sep. 2006.
Echelon, "i.Lon SmartServer," 5 pages, 2007.
Honeywell News Release, "Honeywell's New Sysnet Facilities Integration System for Boiler Plant and Combustion Safety Processes," 4 pages, Dec. 15, 1995.
Honeywell, "Excel Building Supervisor-Integrated R7044 and FS90 Ver. 2.0," Operator Manual, 70 pages, Apr. 1995.
Honeywell Home and Building Control Bulletin, "Introduction of the S7350A Honeywell WebPAD Information Appliance," 2 pages, Aug. 29, 2000; Picture of WebPad Device with touch screen, 1 Page; and screen shots of WebPad Device, 4 pages.
Honeywell, Excel 15B W7760B Building Manager Release 2.02.00, Installation Instructions, 28 pages, Dec. 2004.
Honeywell, The RapidZone Solution, Excel 5000 Open System, Application Guide, 52 pages, Jan. 2004.
"Remote Building Monitoring and Operations Home Page," 5 pages, prior to Aug. 27, 2007.
"Carrier: i-Vu CCN," 1 page, printed Mar. 11, 2008.
Carrier: 33CSCCNWEB-01 CCN Web Internet Connection to the Carrier Comfort Network, 1 page, printed Mar. 11, 2008.
"Products," 5 pages, printed Jul. 3, 2007. http://www.docs.hvacpartners.com/idc/groups/public/documents/techlit/gs-controls-ivuccn.rtf.
Lightstat Incorporated, "Internet Programmable Communicating Thermostats," 1 page, printed Mar. 13, 2007. http://www.lightstat.com/products/istat.asp.
Sharp, "Actius RD3D Desktop Replacement Notebook with Industry-Breakthrough 3D Screen," 1 page, printed Jun. 16, 2005. http://www.sharpsystems.com/products/pc_notebooks/actius/rd/3d/.
"Lights on a Wireless Lighting Control System," 11 pages, printed Mar. 22, 2007 http://www2.sims.berkeley.edu/courses/is213/s06/projects/lightson;final.html.
I.Lon 100e3 Internet Server, 1 page, prior to Aug. 27, 2007.
I.Lon, SmartServer, 2 pages, prior to Aug. 27, 2007.
I-stat, Demo Screen Shots, 9 pages, printed Mar. 13, 2007.
I-stat, The Internet Programmable Thermostat, 2 pages, prior to Aug. 27, 2007.
Ball, "Green Goal of 'Carbon Neutrality' Hits Limit," TheWall Street Journal, 7 pages, Dec. 30, 2008.
Network Integration Engine (NIE), Johnson Controls, 3 pages, Nov. 9, 2007.
Network Integration Engine (NIE), Product Bulletin, Johnson Controls, pp. 1-11, Jan. 30, 2008.
Kourti, "Process Analysis and Abnormal Situation Detection: From Theory to Practice," IEEE Control Systems Magazine, p. 10-25, Oct. 2002.
Mathew, "Action-Oriented Benchmarking, Using CEUS Date to Identify and Prioritize Efficiency Opportunities in California Commercial Buildings," 26 pages, Jun. 2007.
Morrison et al., "The Early Event Detection Toolkit," Honeywell Process Solutions, 14 pages, Jan. 2006.
Narang, "WEBARC: Control and Monitoring of Building Systems Over the Web," 53 pages, May 1999.
Ubiqisense: "UbiqiSense Social Distancing Monitoring and Alert Solutions," May 13, 2020, XP055885698, retrieved from Internet: URL:https://ww.youtube.com/watchZv=BagkA1durps [retrieved on Dec. 31, 2022] (2 pages).
Anonymous: "Honeywell Deploys Video Analytics and AI to Help Building Owners Comply with Social Distancing and Mask Guidelines," Sep. 8, 2020, pp. 1-3, XP055885117, retrieved from the Internet: URL:https://ww.honeywell.com/us/en/press/2020/09/honeywell-deploys-video-analytics-and-ai-to-help-building-owners-comply-with-social-distancing and mask-guidelines [retrieved on Jan. 28, 2022] (1 pg.).
Honeywell ' S: "Operator's Guide MAXPRO Video Management System R670", Apr. 20, 2021, pp. 1-295, XP055885724, Retrievied from the Internet: URL:https://www.security.honeywell.com/product-repository/maxpro-vms [retrieved on Jan. 31, 2022] (16 pgs).
Extended European Search Report, EP Application No. 21197272.4, dated Feb. 10, 2022 (11 pgs.).
Olken et al., "Object Lessons Learned from a Distributed System for Remote Building Monitoring and Operation," ACM SIGPLAN Notices, vol. 33, No. 10, pp. 284-295, Oct. 1998.
Proliphix, Inc., "Proliphix IP Devices: HTTP API," 28 pages, Jan. 23, 2006.
Proliphix, Inc., "Remote Management User Guide," 12 pages, prior to Aug. 27, 2007.
Rogan et al., "Smart and Final Food Stores: A Case Study in Web Based Energy Information and Collection," Web Based Energy Information and Control Systems: Case Studies and Application, Chapter 6, p. 59-64, 2005.
Sharp, "Actius AL3DU 3D LC Display High Performance 3D Visualization," 2 pages, prior to Mar. 17, 2006.
So et al., "Building Automation on the Information Superhighway," ASHRAE Transactions, vol. 104, Part 2, pp. 176-191, 1998.
So et al., "Building Automation Systems on the Internet," Facilities vol. 15, No. 5/6, pp. 125-133, May/Jun. 1997.
Talon, "Raptor Controller," 6 pages, Oct. 2003.
Talon, "Workstation Software," 4 pages, Nov. 2002.
Trane, "System Programming, Tracer Summit Version 14, BMTW-SVP01D-EN," 623 pages, 2002.
Lucid Design Group, Inc., "Building Dashboard," 2 pages, Printed May 30, 2013.
"America's Largest Managed Security Services Provider Launches Comprehensive, Integrated Covid-19 Safety Program for Office Buildings and Suites," KastleSafeSpaces, 5 pages, May 11, 2020.
"Biometric Door Reader With Body Temperature Detection," Kintronics, 9 pages, accessed May 21, 2020.
"Body Surface Temperature Screening with Alarm Function TVS-200IS/TVS-500IS," Nippon Avionics Co., 3 pages, accessed May 21, 2020.
"BriefCam announces video analytics innovation for contact tracing, physical distancing, occupancy management and face mask detection," BriefCam Ltd, 11 pages, Jun. 5, 2020.
"Thermal Imaging SmartPhone Can Be used for Temperature Screening of People," CAT, 3 pages, accessed Jul. 13, 2020.
"Contact Tracing Now Available on Identiv's Hirsch Velocity Access Control Platform," IDENTIV, 5 pages, May 21, 2020.
Silva et al., "Cough localization for the detection of respiratory diseases in pig houses," ScienceDirect, 7 pages, May 28, 2008.
Oey et al., "Evaluation of Isolation Compliance Using Real Time Video in Critical Care," North Shore University Hospital, 1 page, Oct. 9, 2015.
"Facial Attendace System With Temperature Screening Now in India," IANS, 5 pages, Mar. 19, 2020.
"Plan to Re-Open," EHIGH, 16 pages, accessed Jun. 13, 2020.
"How Smarter AI-Powered Cameras Can Mitigate the Spread of Wuhan Novel," AnyConnect, 22 pages, 2020.
"How to fight COVID-19 with machine learning," DataRevenue, 20 pages, accessed May 25, 2020.
Honeywell, "INNCONTROL 5," 2 pages, Aug. 8, 2018.
"IP Door Access Control," KINTRONICS, 21 pages, 2014.
"Kogniz AI Health Response Platform," KOGNIZ, 9 pages, accessed May 21, 2020.
"Machine Learning Could Check If You're Social Distancing Properly at Work," MIT Technology Review, 7 pages, Apr. 17, 2020.
Punn et al., "Monitoring COVID-19 social distancing with person detection and tracking via fine-tuned YOLO v3 and Deepsort techniques," 10 pages, May 6, 2020.
Burt, "NEC launches dual face biometric and fever detection system for access control," BIOMETRIC Update, 4 pages, May 8, 2020.
"Remote temperature monitoring," AXIS Communication, 10 pages, 2014.

(56) References Cited

OTHER PUBLICATIONS

"FebriEye-AI Based Thermal Temperature Screening System," vehant, 1 page, 2020.
"See the World in a New Way Hikvision Thermal Cameras," HIKVISION, 12 p. 2017.
Allain, "Trying out the iPhone Infrared Camera: The FLIR One," WIRED, 15 pages, 2014.
Dasgupta, "Your voice may be able to tell you if you have Covid," Hindustan Times, 4 pages, Apr. 16, 2020.
Ganguty, "Gurugram-based startup Staqu has modified AI-powered JARVIS to battle coronavirus," YOURSTORY, 7 pages, Mar. 31, 2020.
Trane, "Creating Input/Output Objects," 196 pages, retrieved Jul. 10, 2020.
Trane, "Using the Graphing Control Editor," 181 pages, retrieved Jul. 10, 2020.
Genetec, Feature note, "Dashboards, A comprehensive view of your security and operations", pp. 2, 2019 Genetec Inc.
Johnson Controls Develops Industry-first AI Driven Digital Solution to Manage Clean Air, Energy, Sustainability, Comfort and Cost in Buildings, 7 pages, 2022. Accessed Aug. 29, 2022.
Johnson Controls and Microsoft Announce Global Collaboration, Launch Integration between Open Blue Digital Twin and Azure Digital Twins, 7 pages, 2022. Accessed Aug. 29, 2022.
Open Blue Companion Desktop User Guide, Johnson Controls, 18 pages, 2022.
Open Blue Digital Twin:Designed for Buildings. Infused with AI, Johnson Controls, 17 pages, 2022. Accessed Aug. 29, 2022.
Open Blue Enterprise Manager User Guide, Johnson Controls, Release 3.1, 72 pages, Jan. 28, 2021.
Open Blue Enterprise Manager User Guide, Johnson Controls, Release 4.0, 78pages, Nov. 29, 2021.
Open Blue Location Manager User Guide, Johnson Controls, Release 2.4.7, 28 pages, Jul. 20, 2022.
Open Blue Enterprise Manager, Optimize Building Portfolio Performance with Advanced Data Analytics and AI, Johnson Controls, 20 pages, Accessed Aug. 29, 2022.
Open Blue Platform, Make Smarter, Faster, More Data-Driven Decisions, Johnson Controls, 15 pages, 2022. Accessed Aug. 29, 2022.
Open Blue, Now, Spaces have Memory and Identity, Johnson Controls, 20 pages, 2022. Accessed Feb. 10, 2022.
Open Blue Enterprise Manager User Guide, Johnson Controls, 108 pages, Release 4.1.3, 2022, Accessed Aug. 29, 2022.
Risbeck et al.; "Modeling and Multiobjective Optimization of Indoor Airborne Disease Transmission Risk and Associated Energy Consumption for Building HVAC Systems," Energy and Buildings, vol. 253, 24 pages, 2021.
Sinha et al.; "Balance Infection Risk, Sustainability and Comfort with Open Blue," Johnson Controls, 2 pages, 2021.
Building Automation System in Michigan, Johnson Heating and Cooling, L.L.C., www.cooljohnson.com/Building-Automation-Systems-Michigan/Macomb-County-Michigan/Building-Automation-Confidential-Customer.html, 4 pages, Accessed Nov. 21, 2022.
Building Automation System Waterford Michingan 48328 JLA, Johnson Heating and Cooling L.L.C., www.cooljohnson.com/Building-Automation-Systems-Michigan/Waterford-Michigan/Building-Automation-System-JLA.html, 3 pages, Accessed Nov. 21, 2022.
Building Automation Systems Waterford Michigan 48330 SJMO, Johnson Heating and Cooling, L.L.C., www.cooljohnson.com/Building-Automation-Systems-Michigan/Waterford-Michigan/Building-Automation-Systems-SJMO.html, 2 pages, Accessed Nov. 21, 2022.
Building Automation Systems Waterford Michigan 48329 WIM, Johnson Heating and Cooling L.L.C., www.cooljohnson.com/Building-Automation-Systems-Michigan/Building-Automation-Systems-WIM.html, 3 pages, accessed Nov. 21, 2022.
Building Automation Clawson Michigan 2.0, Johnson Heating and Cooling L.L.C., www.cooljohnson.com/Building-Automation-Systems-Michigan/Clawson-Michigan/Building-Automation-Clawson-Manor-2.html, 6 pages, Accessed Nov. 21, 2022.
Building Automation in Detroit—Mosaic Christian, Johnson Heating and Cooling L.L.C., www.cooljohnson.com/Building-Automation-Systems-Michigan/Detroit/Mosaic-Christian.html, 5 pages, Accessed Nov. 21, 2022.
Building Automation in Michigan—Divine Grace, Johnson Heating and Cooling L.L.C., www.cooljohnson.com/Building-Automation-Systems-Michigan/Oakland-County-Michigan/Building-Automation-Divine-Grace.html, 3 pages, Accessed Nov. 21, 2022.
Building Automation System Plymouth, Michigan, Johnson Heating and Cooling L.L.C., www.cooljohnson.com/Building-Automation-Systems-Michigan/Plymouth-Michigan/Building-Automation-System-Plymouth-Michigan.html, 8 pages, Accessed Nov. 21, 2022.
Building Automation Systems Shelby Michigan 48316 SG, Johnson Heating and Cooling L.L.C., www.cooljohnson.com/Building-Automation-Systems-Michigan/Shelby-Township-Michigan/Building-Automation-Systems-SG.html, 3 pages, Accessed Nov. 21, 2022.
Building Automation System St. Clair County, Michigan, Johnson Heating and Cooling L.L.C., www.cooljohnson.com/building-Automation-Systems-Michigan/St-Clair-Michigan/Building-Automation-system-St-Clair-Michigan.html, 4 pages, Accessed Nov. 21, 2022.
Building Automation System Troy Michigan Oakland Mall, Johnson Heating and Cooling L.L.C., www.cooljohnson.com/Building-Automation-Systems-Michigan/Troy Michigan/Building-Automation-System-Oakland-Mall.html, 4 pages, Accessed Nov. 21, 2022.
Building Automation System Waterford Michigan 48327 Excel, Johnson Heating and Cooling L.L.C., www.cooljohnson.com/Building-Automation-Systems-Michigan/Waterford-Michigan/Building-Automation-System-excel.html, 2 pages, Accessed Nov. 22, 2022.
Building Automation System Romeo Michigan 48065 RomeoPR, Johnson Heating and Cooling, L.L.C., www.cooljohnson.com/Building-Automation-Systems-Michigan/Romeo-Michigan/Building-Automation-System-RomeoPR. html, 2 pages, Accessed Nov. 21, 2022.
Johnson, Jr., "Cooling Logic™: Changing the Way You Cool," Johnson Solid State, LLC, 12 pages, Nov. 7, 2018.
Building Automation System Clawson Michigan Clawson Manor, Johnson Heating and Cooling L.L.C., www.cooljohnson.com/building-Automation-Systems-michigan/clawson-Michigan/building-Automation-System-Clawson-Manor.html, 3 pages, Accessed Nov. 21, 2022.
Johnson, Jr., "CoolingLogic™ A Method to increase HVAC System Efficiency And Decrease Energy Consumption," A White Paper, Johnson Solid State, L.L.C., 51 pages, Sep. 24, 2016.
Johnson, Jr., "CoolingLogic™: Mosaic Christian Church a Case Study," 140 pages, Feb. 2, 2019.
Title: CoolingLogic A Method to Increase HVAC System Efficiency And Decrease Energy Consumption Author: David L. Johnson Jr. Published online on or about: Sep. 24, 2016 Available online at: CoolingLogic.com Printed copy delivered to Honeywell on Dec. 2, 2016.†
Author: David Johnson Title of the publication: Building Automation Systems St Clair pp. 3 Published online on or about: Nov. 16, 2015 Available online at: www.cooljohnson.com/ Building-Automation-Systems-Michigan/St-Clair-Michigan/Building-Automation-System-St-Clair-Michigan.html Evidence of publication could likely be found using the waybackmachine, if desired.†

\* cited by examiner
† cited by third party

Healthy Building Dashboard

ALL KPI'S　AIR QUALITY KPI'S　MINIMIZE RISK KPI'S　ZONE SUMMARY

Zones Overview

| STATUS | ZONE NAME | TEMP | HUMIDITY | OA FLOW | CO2 | CO | TVOC | OCC | |
|---|---|---|---|---|---|---|---|---|---|
| | RECOMMENDED VALUES | 68 - 74 °F | 40 - 60%RH | 900 CFM | <800 PPM | <20 PPM | <0.5mg/m3 | <50% | |
| OUT OF RANGE | Zone 1 - Reception | 72.6 °F | 60.7% RH | 1,011 cfm | 770 ppm | 20.0 ppm | 0.04 mg/m3 | 40% | |
| OUT OF RANGE | Zone 2 - 1st Floor Main Lab | 74.6 °F | 53.1% RH | 843 cfm | 531 ppm | 22.1 ppm | 2.88 mg/m3 | 28% | |
| OUT OF RANGE | Zone 3 - 2nd Floor R&D Lab | 74.4 °F | 52.1% RH | 1,065 cfm | 505 ppm | 24.6 ppm | 2.09 mg/m3 | 46% | |
| GOOD | Zone 4 - 3rd Floor East Wing | 73.0 °F | 53.6% RH | 1,181 cfm | 786 ppm | 12.4 ppm | 0.01 mg/m3 | 39% | |
| OUT OF RANGE | Zone 5 - 3rd Floor West Wing | 74.7 °F | 51.4% RH | 1,066 cfm | 507 ppm | 18.1 ppm | 0.04 mg/m3 | 41% | |
| OUT OF RANGE | Zone 6 - 4th Floor East Wing | 74.5 °F | 57.9% RH | 1,162 cfm | 534 ppm | 17.0 ppm | 0.04 mg/m3 | 16% | |
| OUT OF RANGE | Zone 7 - 4th Floor West Wing | 74.3 °F | 52.7% RH | 1,176 cfm | 575 ppm | 13.0 ppm | 0.04 mg/m3 | 23% | |
| GOOD | Zone 8 - 5th Floor East Wing | 72.5 °F | 53.7% RH | 1,145 cfm | 413 ppm | 16.7 ppm | 2.9 mg/m3 | 19% | |
| OUT OF RANGE | Zone9 - 5th Floor West Wing | 72.5 °F | 52.1% RH | 891 cfm | 556 ppm | 16.7 ppm | 0.04 mg/m3 | 55% | |
| GOOD | Zone 10 - 6th Floor East Wing | 70.0 °F | 52.0% RH | 1,165 cfm | 432 ppm | 16.3 ppm | 0.04 mg/m3 | 24% | |

FIG. 7

| PRIORITY | DATE & TIME | LOCATION | SOURCE | ALARM TYPE | LIVE VALUE |
|---|---|---|---|---|---|
| ⚠ H00 | 8/15/2020 10:43:37 | HB_Z01 | HB_Zone_Z01 | Zone-01 Temperature | 75.00 |
| ⚠ H00 | 8/15/2020 10:43:25 | HB_Z02 | HB_Zone_Z02 | Zone-01 Temperature | 73.98 |
| ⚠ H00 | 8/15/2020 10:43:24 | HB_Z03 | HB_Zone_Z03 | Zone-03 AHU Temperature 01 | 76.00 |
| ⚠ H00 | 8/15/2020 10:41:54 | HB_Z02 | HB_Zone_Z02 | Zone-02 Humidity | 51.73 |

Pop-up menu (216):
- ✓ Acknowledge alarm
- 🔍 Detail display
- Associated display
- Alarm Help

FIG. 9

| PRIORITY | DATE & TIME | LOCATION | SOURCE | ALARM TYPE | LIVE VALUE | LIMIT |
|---|---|---|---|---|---|---|
| U00 | 8/13/2020 8:21:00 | Facility | HB_C | Camera-01 Thermal Alarm | Alarm | |
| H00 | 8/16/2020 10:17:11 | HB_Z03 | HB_Z | Zone-03 AHU Temperature 01 | 74.14 | 74.00 |
| H00 | 8/16/2020 10:17:05 | HB_Z01 | HB_Z | Zone-01 Humidity | 62.00 | 60.00 |
| H00 | 8/16/2020 10:17:00 | HB_Z01 | HB_Z | Zone-01 Temperature | 73.94 | 74.00 |

Menu options:
- Acknowledge alarm
- Detail display
- Associated display — Navigate to the associated display of the selected alarm
- Alarm Help 280, 282, 284, 286

| ◁ ◁ | 1 | of 1 | ▷ ▷| | ↻ | ⊕ | | #HB | 🏠 ⌂ ⚠ ☀ 📅 🖼 🖼 ⊗ ≪ ◎ 🔍 🖴 | | 100% | ▽ | | Zoom To Fit ▼ | Command |

| 🖫 ▼ | | ⌖ | | | | Find | Next |

Incident Detail Report
Displays a list of incidents that have occurred on the system and their details

Report Criteria
Incident ID  21

Number of incidents found: 1

Summary
| Incident ID: | 21 |
| Incident Type: | Isolation of Facility |
| Priority: | High |
| Owner: | .\Administrator |
| Location: | /Facility |
| Source: | HB_Zone10_Temp |
| Status: | Open |
| Age: | 4d 14h 0m 50s |
| Description: | This procedure must be followed to isolate person if a high temperature detected in Thermal Screening |

Incident Life Cycle
| State | User Name | Time |
| Incident raised. | .\mngr | 8/13/2020 5:37:23 AM |
| Incident ownership assigned to .\Administrator. | | 8/13/2020 6:22:20 AM |

General Comments
| Comment | User Name | Time |
| Workflow 21 initiated - Thermal Screening. | .\mngr | 8/13/2020 5:37:23 AM |

DASHBOARD FOR TRACKING HEALTHY BUILDING PERFORMANCE

RELATED APPLICATION

This application claims the benefit of U.S. Provisional Patent Application Ser. No. 63/085,921, filed Sep. 30, 2020, which is incorporated herein by reference.

TECHNICAL FIELD

The present disclosure pertains to monitoring building performance. More particularly, the present disclosure pertains to monitoring compliance with healthy building standards.

BACKGROUND

Coronavirus disease 2019 (COVID-19) is an infectious disease caused by severe acute respiratory syndrome coronavirus 2 (SARS-CoV-2). COVID-19 is one of many infectious diseases transmitted via airborne and/or other particles. In some cases, it may be difficult to mitigate the spread of infectious diseases, particularly diseases transmitted through airborne and/or other particles, at indoor facilities (e.g., buildings, department stores, warehouses, plants, factories, refineries, airports, laboratories, school buildings, theaters, etc.) due to the indoor environment, proximity of occupants, and/or other factors. Often, these indoor facilities have various building automation systems (e.g., heating, ventilation, and air conditioning (HVAC) systems, surveillance systems, security systems, energy management systems, etc.) to control environmental conditions of the indoor facility and/or monitor occupancy. A need remains for ways to monitor how well a building or other facility is performing with respect to meeting healthy building guidelines.

SUMMARY

The present disclosure relates to a monitoring compliance with prescribed guidance, and more particularly, to monitoring compliance of a facility such as a building with healthy building guidelines that are intended to reduce changes of infectious disease spread within the facility.

In an example, a method of monitoring building compliance with healthy building guidelines, where the healthy building guidelines specify desired ranges for each of a plurality of different parameters, includes obtaining current parameter values for a plurality of different parameters from a plurality of sensors disposed within a plurality of different zones of a building. For each of the parameters, the current parameter value received from each of the plurality of different zones is compared with a corresponding healthy building range for that parameter as specified by the healthy building guidelines. A healthy building dashboard is displayed that includes a summary that shows, for each of the plurality of different parameters, how many zones of the plurality of different zones of the building are within the corresponding healthy building range for that parameter and/or how many zones of the plurality of different zones are not within the corresponding healthy building range for that parameter.

In another example, a method of monitoring building compliance with healthy building guidelines, where the healthy building guidelines specify desired ranges for each of a plurality of different parameters, includes receiving parameter values for a plurality of different parameters in a building. The current values for each of the plurality of different parameters are compared to a corresponding healthy building range specified in the healthy building guidelines to help reduce the spread of disease in the building. A healthy building dashboard is displayed on a display that indicates for each of the plurality of different parameters whether any areas of the building are not within the healthy building range for that parameter. In response to a user request, additional information is displayed on the display that pertains to the areas of the building for which one or more of the parameters are outside of the healthy building range for that parameter.

In another example, a non-transient, computer-readable storage medium stores instructions that when executed by a processor cause the processor to receive parameter values for a plurality of different parameters in a building over time, compare current values for each of the plurality of different parameters to a healthy building range specified for each of the plurality of different parameters and display a dashboard on a display that indicates for each of the plurality of different parameters whether any areas of the building are not within the healthy building range for that parameter. In response to a user request, additional information may be displayed on the display that pertains to the areas of the building for which one or more of the parameters are outside of the healthy building range for that parameter.

The preceding summary is provided to facilitate an understanding of some of the features of the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following description of various illustrative embodiments of the disclosure in connection with the accompanying drawings, in which:

FIGS. 4 through 21 are screen captures showing illustrative screens that may be displayed by the illustrative system of FIG. 1.

Figure 1:
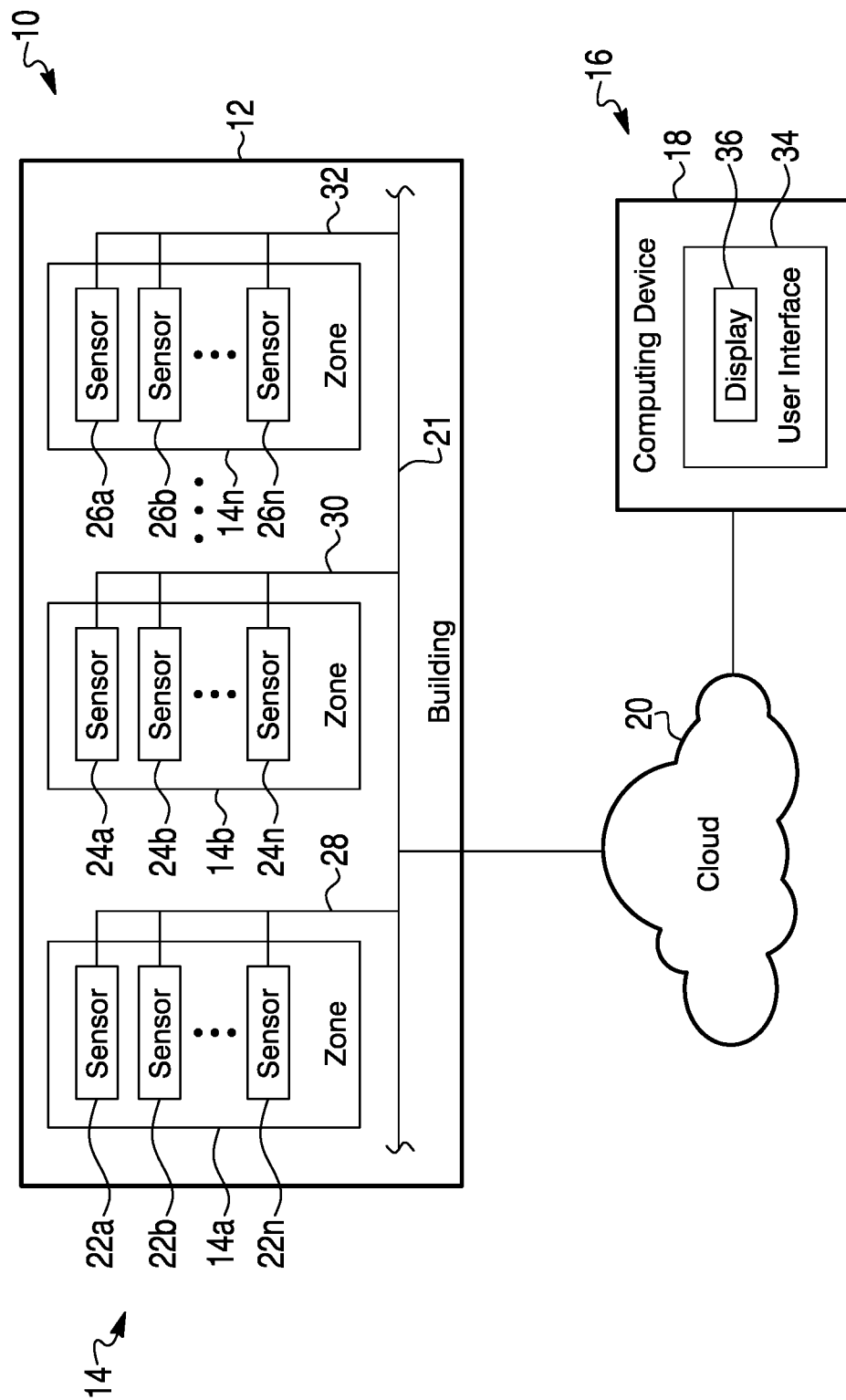
FIG. 1 is a schematic view of an illustrative system for monitoring building compliance with healthy building guidelines.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings wherein like reference numerals indicate like elements. The drawings, which are not necessarily to scale, are not intended to limit the scope of the disclosure. In some of the figures, elements not believed necessary to an understanding of relationships among illustrated components may have been omitted for clarity.

All numbers are herein assumed to be modified by the term "about", unless the content clearly dictates otherwise. The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic may be applied to other embodiments whether or not explicitly described unless clearly stated to the contrary.

Facilities often include building automation systems (e.g., heating, ventilation, and air conditioning (HVAC) systems, surveillance systems, security systems, energy management systems, etc.). Various organizations worldwide (e.g., government organizations, educational organizations, etc.) have provided guidelines on how to operate building automation system to reduce risk of disease transmissions within facilities. Similarly, various organizations worldwide have provided guidelines on how occupants of a facility and monitoring occupancy can reduced risk of disease transmission. Other guidelines relating to facilities and transmission of infectious disease are contemplated and may be adapted and used, depending on the facility.

It can be difficult for facility managers to assess performance of their facilities, occupants, etc. against guidance (e.g. guidelines, rules, etc.). In some cases, the guidance may specify desired environmental conditions and desired occupancy/occupant behavior to help reduce or mitigate risk of disease transmission in a facility. Additionally, in view of various guidelines from various organizations, it has been difficult for facility managers to assess whether their facilities have the necessary sensor devices and/or other suitable sensing or monitoring equipment to accurately judge and/or reduce the risk of disease transmission.

This disclosure provides methods and systems for assessing a facilities compliance with various guidelines related to reducing risk of infectious disease (e.g., COVID-19, Ebola, influenza, common cold, airborne diseases, and/or other infectious diseases) transmissions. Sensing devices of existing building automation systems and/or other suitable sensing devices may be utilized. In some cases, methods and systems are provided to help facility managers identify when additional sensors, cameras, and/or other equipment may help in mitigating risk of transmitting infectious diseases in their facility, and in some cases, may quantify how much such additional equipment may help mitigate the risk of transmission of infectious diseases in their facility.

The techniques and/or systems disclosed herein may provide displays offering facility managers easily understandable performance metrics of a facility and/or facility occupants' against a set of infectious disease guidelines. The metrics may incorporate and/or be based on knowledge of a facility location (e.g., geographic location), knowledge of a facility size, knowledge of a facility floorplan, knowledge of sensing devices at a facility, knowledge of common HVAC system capability, and parameters, adjustable values or weights that may be tuned based on climate, building characteristics, and evolving knowledge (e.g., guidelines, studies, laws, etc.) related to disease transmission, etc.

FIG. 1 is a schematic block diagram of an illustrative system 10 for monitoring building compliance with healthy building guidelines. Healthy building guidelines may, for example, include infectious disease guidance. Infectious disease guidance may include recommendations related to values, counts, percentages, and/or other measures of one or more of relative humidity in a facility, $CO_2$ concentration in a facility, air change rates in a facility, occupancy in a facility, particulate matter concentrations in a facility, total volatile organic compound (TVOC) concentrations in a facility, a maximum occupancy level in a facility or a zone in a facility, maximum occupancy density in a facility, a number of crowd incidents per day in the facility, a percent of health related standard operating procedure actions that have been closed by an facility operator, mask compliance in a facility, elevated body temperature incidents in the facility, number of people potentially exposed to an infected individual in the facility determined via contact tracing, and/or recommendations or actions related to one or more other suitable factors affecting disease transmission within a facility.

The illustrative system 10 of FIG. 1 includes a building 12. It will be appreciated that the building 12 may represent a single building, or a collection of buildings. In some instances, the building 12 may represent a portion of a facility. Illustrative but non-limiting examples of buildings 12 include buildings, department stores, warehouses, plants, factories, refineries, airports, laboratories, office buildings, school buildings, theaters, arenas, stadiums, hotels, dorms, lecture halls, restaurants, etc. The building 12 may be considered as being divided into zones 14 that are individually labeled as 14a, 14b through 14n. Each zone 14 may represent a room or collection of rooms in the building 12. Each zone 14 may represent a floor of the building 12. Each zone 14 may represent particular regions within the building 12 that may not correspond directly to a particular room and/or a particular floor of the building 12. In some instances, the zones 14 may correspond to Heating, Ventilating and Air Conditioning (HVAC) system zones. In some cases, the zones 14 may represent divisions of the building 12 based upon use of various parts of the building 12. For example, a particular zone 14 may represent a collection of offices within the building 12 while another zone 14 may represent warehouse space. Another zone 14 may represent part or all of a parking garage, for example. It will be appreciated that in this, the ventilation and other needs of these various zones 14 may vary, sometimes considerably, based on how they are being utilized. Accordingly, it can make sense to define zones in accordance with how the various parts of the building 12 are being utilized.

The illustrative system 10 further includes a computing system 16. As illustrated, the computing system 16 includes a computing device 18 and one or more cloud servers 20. The building 12 includes a building network 21 that enables devices within the building 12 to communicate with the computing system 16, and in some cases with each other. It will be appreciated that in some instances the computing device 18 may be disposed within the building 12 and may itself be in communication with the building network 21 without requiring any intervening servers such as but not limited to the cloud server 20. The computing device 18 may itself be manifested within the cloud server 20. In some cases, the computing device 18 may be and/or may be part of, for instance, a smart phone, a tablet, a personal digital assistant (PDA), a personal computer, a beacon, a camera, a display device, a video recorder, a network component, a server, and/or other suitable computing device. In some cases, the computing device 18 may be distributed amount two or more devices.

As illustrated, the building 12 includes a number of sensors disposed within each of the zones 14. For example, the zone 14a includes a sensor 22a, a sensor 22b and through a sensor 22m. The zone 14b includes a sensor 24a, a sensor 24b and through a sensor 24m. The zone 14n includes a sensor 26a, a sensor 26b and through a sensor 26m. It will be appreciated that each of the sensors 22, 24, 26 may measure or detect any of a variety of different measures that are related to one or more parameters that may be part of the healthy building guidelines. The sensors 22, 24, 26 may include one or more of occupancy sensors, video cameras, still cameras, identification card readers, control signal monitors (e.g., to monitor when and/or how devices affecting infectious disease are used, such as UV lights, air exchangers, fans, etc.), air sensors, humidity sensors, temperature sensors, $CO_2$ (carbon dioxide) sensors, CO (carbon monoxide) sensors, thermostats, particulate matter sensors, TVOC (total volatile organic compound) sensors, thermometers, infrared sensors, pressure sensors (e.g., to monitor and/or effect pressure zones configured to exchange air in a specified zone in a facility), etc.

In the example show, the sensors 22a, 22b through 22m are able to communicate with the building network 21 and hence with the computing system 16 via a zone network 28. The sensors 24a, 24b through 24m are able to communicate with the building network 21 and hence with the computing system 16 via a zone network 30. The sensors 26a, 26b through 26m are able to communicate with the building network 21 and hence with the computing system 16 via a zone network 32. In some cases, signals from each of the sensors 22, 24, 26 are communicated to the computing device 18, either directly or via the cloud server 20. The computing device 18 includes a user interface 34 that may be used to provide instructions and other information to the computing device 18 and/or to receive information from the computing device 18. The user interface 34 may include any desired type of data entry equipment, such as but not limited to a keyboard, a mouse, a touch pad, a drawing pad and the like. The user interface 34 may include a display 36 that can be used to display information. The display 36 may include one or more separate monitors, each of the one or more separate monitors being addressable by the computing device 18.

In some cases, the display 36 may be used to display a dashboard that enables a user to quickly and easily ascertain how the building 12 is performing relative to various healthy building guidelines. Such a dashboard may display current values of various parameters measured or otherwise indicated by the sensors 22, 24, 26, and may include comparisons of the current values of those parameters with healthy building ranges for those parameters. Subsequent Figures will provide examples of dashboards that may be displayed on the display 36.

Figure 2:
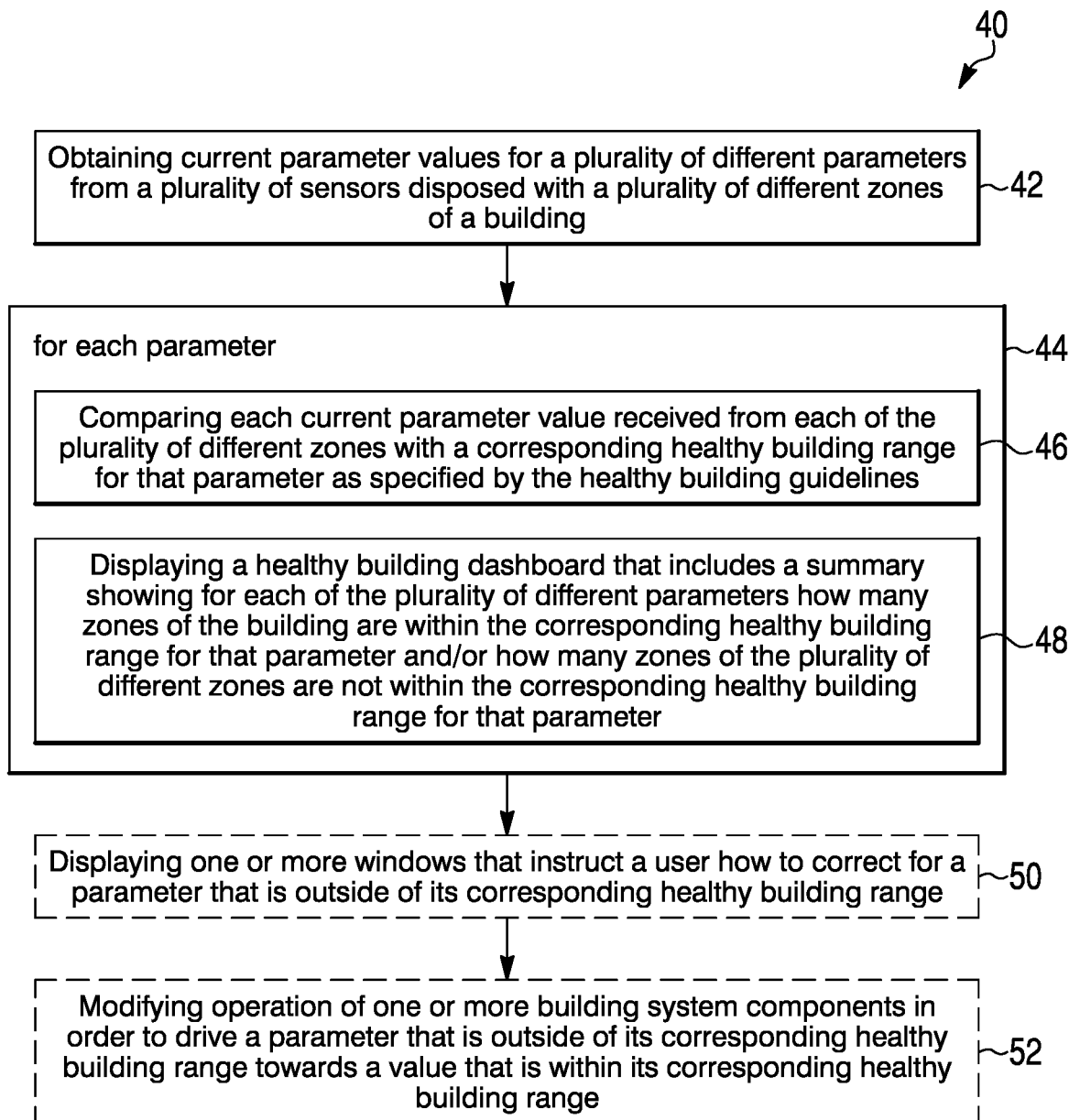
FIG. 2 is a flow diagram showing an illustrative method of monitoring building compliance with healthy building guidelines.

FIG. 2 is a flow diagram showing an illustrative method 40 of monitoring building compliance with healthy building guidelines, where the healthy building guidelines specify desired ranges for each of a plurality of different parameters. Current parameter values may be obtained for each of a plurality of different parameters from a plurality of sensors (such as the sensors 22, 24, 26) that are disposed within a plurality of different zones (such as the zones 14) of the building 12, as indicated at block 42. The values for each parameter may be processed, as indicated at block 44. In more detail, each current parameter value received from each of the plurality of different zones may be compared with a corresponding healthy building range for that parameter as specified by the healthy building guidelines, as indicated at block 46. A healthy building dashboard may be displayed that includes a summary that shows, for each of the plurality of different parameters, how many zones of the plurality of different zones of the building are within the corresponding healthy building range for that parameter and/or how many zones of the plurality of different zones are not within the corresponding healthy building range for that parameter, as indicated at block 48. In some cases, at least a region of the dashboard may collect and display only parameters that have a corresponding healthy building range specified by the healthy building guidelines. In some cases, all available parameters that have a corresponding healthy building range specified by the healthy building guidelines are displayed in this region. When so provided, a user may navigate to this region to get a good overall view of building compliance with the relevant healthy building guidelines.

In some instances, and as optionally indicated at block 50, the method 40 may further include displaying one or more windows that instruct a user how to correct for a parameter that is outside of its corresponding healthy building range. In some instances, and as optionally indicated at block 52, the method 40 may further include modifying operation of one or more building system components in order to drive a parameter that is outside of its corresponding healthy building range towards a value that is within its corresponding healthy building range. While not expressly illustrated, it will be appreciated that the building 12 may include a variety of building systems such as but not limited to an HVAC system, and the HVAC system may include heating, cooling and/or ventilating components that may be used to alter a current value of a parameter (e.g. by changing a set point, opening a damper or valve, activating a fan, changing a fan speed, etc.). In some cases, the healthy building dashboard may also include a summary of healthy building alarms, wherein each health building alarm corresponds to a parameter in a zone (such as one of the zones 14) that falls outside or otherwise does not meet its corresponding healthy building range.

One of the plurality of different parameters for which a current parameter value may be compared to a corresponding healthy building range includes air temperature. The healthy building range for air temperature may correspond to a range of, for example, 68 to 74 degrees Fahrenheit. In some cases, air temperatures within this range can help to reduce the spread of disease within the building 12. It will be appreciated that these temperatures also generally correspond to those that are considered to be comfortable by a majority of people, although the upper temperature limit of 74 degrees Fahrenheit may be viewed as lower than historically preferred for energy savings, especially for summertime air conditioning.

Another of the plurality of different parameters for which a current parameter value may be compared to a corresponding healthy building range includes relative humidity. The healthy building range for relative humidity may correspond to, for example, a range of 40 to 60 percent relative humidity. In some cases, relative humidity values within this range can help to reduce the spread of disease within the building 12. In some cases, the next preferred relative humidity is in a range of 60 to 70 percent relative humidity. The next preferred relative humidity is a relative humidity in excess of 70 percent relative humidity. The next preferred is a relative humidity in a range of 30 to 50 percent relative humidity. A least preferred relative humidity is a relative humidity that is less than 30 percent relative humidity.

Another of the plurality of different parameters for which a current parameter value may be compared to a corresponding healthy building range includes carbon dioxide concentration. The healthy building range for carbon dioxide concentration may correspond to a carbon dioxide concentration of less than 800 parts per million (ppm). It will be appreciated that the primary source of carbon dioxide within the building 12 is people exhaling, and thus may be related to a density of occupants within the building. In some cases, a carbon dioxide concentration of less than 800 ppm can help to reduce the spread of disease within the building 12.

Additional examples of different parameters for which a current parameter value may be compared to a corresponding healthy building range include carbon monoxide concentration and total volatile organic compound (TVOC) concentration. The healthy building range for carbon monoxide concentration is less than 20 ppm. The healthy building range for TVOC concentration is less than 0.5 milligrams per cubic meter ($mg/m^3$). It will be appreciated that carbon monoxide and TVOCs are both undesirable, and thus there is a desire to minimize (or even eliminate) detectable concentrations of either. In some cases, a carbon monoxide concentration of less than 20 ppm and/or a TVOC concentration of less than 0.5 $mg/m^3$ can help to reduce the spread of disease within the building 12.

Some parameters for which a current parameter value may be compared to a corresponding healthy building range include parameters that are more behavior-based. An example of this is occupancy percentage. In accordance with healthy building guidelines, there may be a desire to limit relative occupancy of a space such as one or more of the zones 14 within the building 12. Limiting relative occupancy has the impact of increasing relative distances between people over time. While there may be instances in which a first person is too close to a second person, even transiently, it will be appreciated that having relatively fewer people in a particular space will tend to increase the relative distances between them. This can help with achieving social distancing. In some cases, a relative occupancy of less than 50 percent of a specified maximum occupancy may be desired. In some instances, a relative occupancy of less than 25 percent of a specified maximum occupancy may be desired. The specified maximum occupancy may be determined based on one or more characteristics of the particular space, and in some cases may represent the maximum safe allowed occupancy of that space as specified by the fire code of the municipality, state or the like in which the building 12 is located.

In some cases, the healthy building dashboard may include a summary of healthy building security parameters. These healthy building security parameters, which may be considered as additional examples of behavior-based parameters, may include one or more of an occupant temperature compliance parameter that relates to a status of occupant temperature compliance of occupants of the building. This can include an indication of whether occupants within the building have a healthy body temperature as opposed to an elevated body temperature that may be an indication of disease. Individual body temperatures may be estimated, for example, by taking infrared pictures of the individuals using an infrared security camera spaced throughout the building or performing a temperature screening at one or more access points of the building.

Another example of a healthy building security parameter is a mask compliance parameter that relates to a status of mask compliance of occupants of the building with one or more mask guidelines specified by the healthy building guidelines. If people are wearing masks during circumstances that warrant masks, this can help to reduce disease spread. Conversely, people who are not wearing masks during circumstances that warrant masks, this can worsen disease spread. Another example of a healthy building security parameter is a social distancing compliance parameter that relates to a status of social distancing compliance of occupants of the building with one or more social distancing guidelines specified by the healthy building guidelines. Another example of a healthy building security parameter is a maximum occupancy compliance parameter that relates to a status of maximum occupancy compliance of occupants of the building with one or more maximum occupancy guidelines specified by the healthy building guidelines. These are just examples, and additional healthy building security parameters are contemplated. Mask compliance, social distancing and maximum occupancy can each be identified by, for example, performing video analytics on video images captured by security camera spaced throughout the building.

In some cases, the healthy building dashboard may include a zone summary that for each of the plurality of different zones of the building which displays each current parameter value measured within that zone. The zone summary may, for example, highlight any current parameter value in any zone of the plurality of different zones that is currently outside of the corresponding healthy building range for that parameter. In some instances, the zone summary may include a recitation of the corresponding healthy building range for each of the parameters. In some cases, the zone summary may include links that when selected by a user display additional information. The additional information may include numerical values for one or more of the plurality of different parameters displayed over time to show trends. The additional information may include instructions as to how to improve the numerical values for one or more of the plurality of different parameters (e.g. change a set point, send a notification to individual occupants, add a sensor or other equipment such as a humidifier to the building facility management system, etc.). In some cases, the additional information may include a Standard Operating Procedure (SOE) that be define a set of steps that the operator should take to address the situation.

Figure 3:
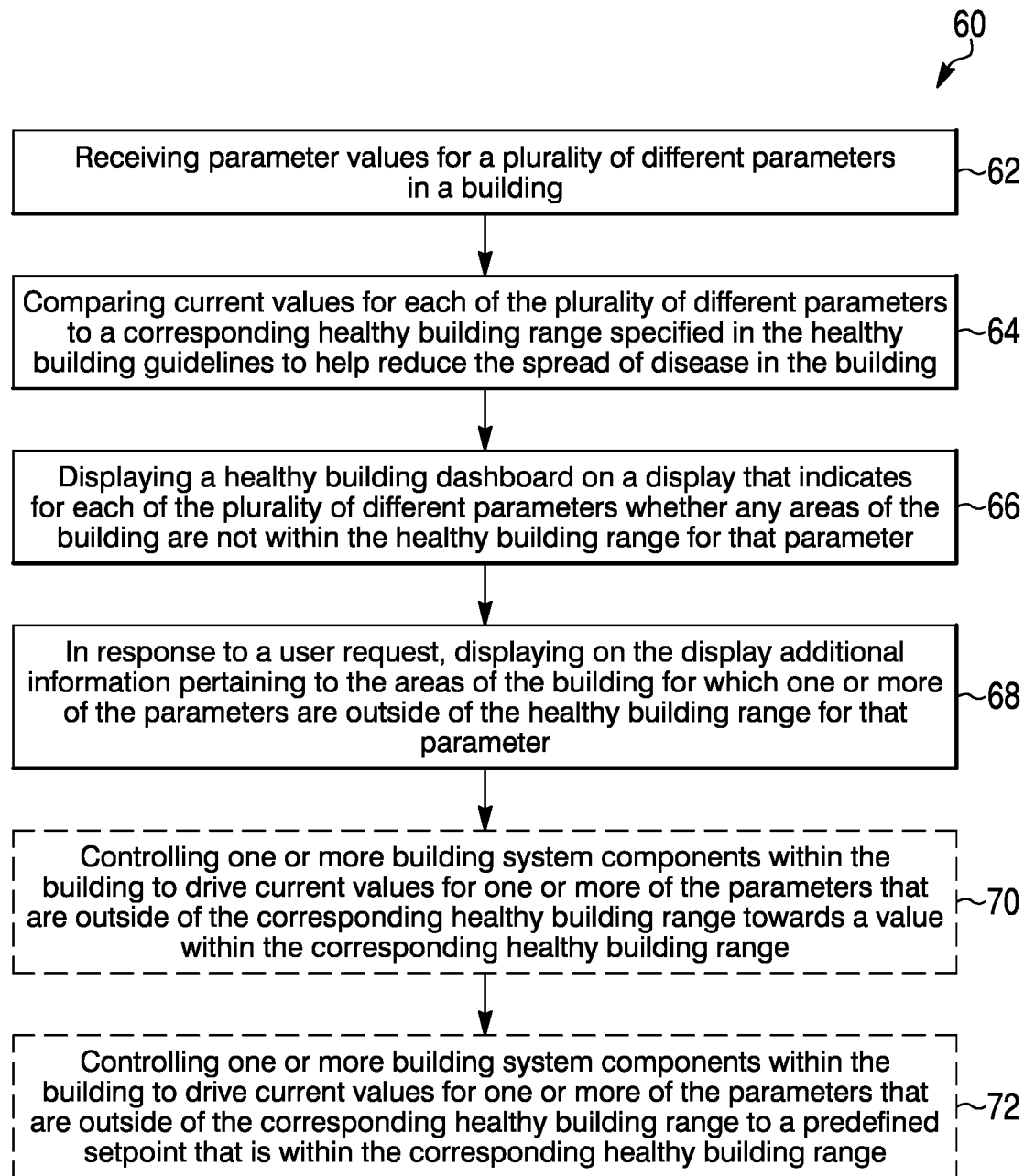
FIG. 3 is a flow diagram showing an illustrative method of monitoring building compliance with healthy building guidelines.

FIG. 3 is a flow diagram showing an illustrative method 60 of monitoring building compliance with healthy building guidelines, where the healthy building guidelines specify desired ranges for each of a plurality of different parameters. Parameter values for a plurality of different parameters in a building (such as the building 12) are received, as indicated at block 62. The current values for each of the plurality of different parameters are compared to a corresponding healthy building range specified in the healthy building guidelines to help reduce the spread of disease in the building, as indicated at block 64. A healthy building dashboard is displayed on a display that indicates for each of the plurality of different parameters whether any areas of the building are not within the healthy building range for that parameter, as indicate at block 66. In response to a user request, additional information is displayed on the display that pertains to the areas of the building for which one or more of the parameters are outside of the healthy building range for that parameter, as indicated at block 68.

In some instances, and as optionally indicated at block 70, the method 60 may further include controlling one or more building system components within the building to drive current values for one or more of the parameters that are outside of the corresponding healthy building range towards a value within the corresponding healthy building range (e.g. change a set point, send a notification to individual occupants, add a sensor or other equipment such as a humidifier to the building facility management system, etc.). In some cases, and as optionally indicated at block 72, the method 60 may further include controlling one or more building system components within the building to drive current values for one or more of the parameters that are outside of the corresponding healthy building range to a predefined setpoint that is within the corresponding healthy building range.

FIGS. 4 through 21 provide illustrative screen shots showing a variety of healthy building dashboards that may be displayed, for example, on the display 36 of the computing device 18. In these dashboards, it will be appreciated that the parameters are sometimes referred to as KPIs, or Key Performance Indicators. The dashboards described herein can for example display all KPIs, including Air Quality KPIs and Healthy Building Security KPIs. In this, Security KPIs are those parameters that refer to behavioral-related parameters such as body temperature, mask compliance, intrusion detection, social distancing and occupancy. The dashboards may display only Air Quality KPIs. The dashboards may display only Healthy Building KPIs. The dashboards may display only zone summaries. These are just examples.

Figure 4:
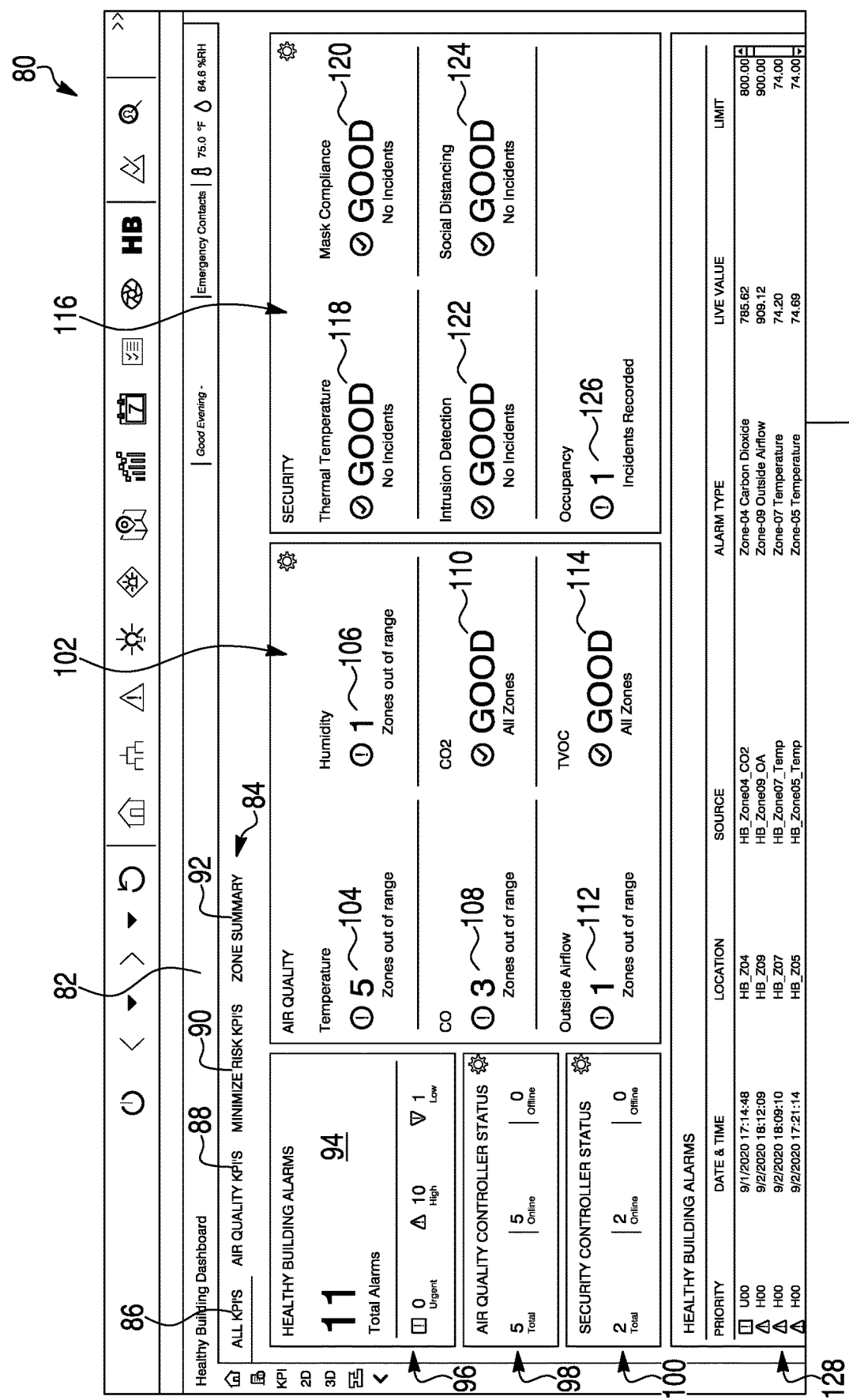

FIG. 4 shows a screen 80 that includes a dashboard 82. The dashboard 82 includes a header 84 that includes an icon 86 for ALL KPIS, an icon 88 for AIR QUALITY KPIS, an icon 90 for MINIMIZE RISK KPIS (security KPIs) and a ZONE SUMMARY icon 92. As can be seen, the icon 86 for ALL KPIS is underlined or otherwise highlighted, indicating that the dashboard 82 is currently displaying all available KPIs. A user can tab between the icons 86, 88, 90, 92 included in the header 84 by clicking on or otherwise selecting a desired icon 86, 88, 90, 92. The dashboard 82 includes a HEALTHY BUILDING ALARMS panel 94 that provides summary information regarding current alarms. The HEALTHY BUILDING ALARMS panel 94 includes a summary section 96 that illustrates a current number of urgent alarms, a current number of high priority alarms and a current number of low priority alarms. The HEALTHY BUILDING ALARMS panel 94 also shows a total number of alarms. The HEALTHY BUILDING ALARMS panel 94 also includes an AIR QUALITY CONTROLLER STATUS section 98 that identifies how many air quality controllers are present and online. The HEALTHY BUILDING ALARMS panel 94 also includes a SECURITY CONTROLLER STATUS section 100 that identifies how many security controllers are present and online.

The illustrative dashboard 82 includes an AIR QUALITY panel 102 that indicates for each of a number of air quality parameters (or KPIs), whether the current values for these parameters within any of the zones are in range or out of range, along with a total number of zones that are in range or out of range. The AIR QUALITY panel 102 includes a temperature section 104, a humidity section 106, a CO section 108, a $CO_2$ section 110, an Outside Airflow section 112 and a TVOC section 114. As indicated, there are a total of five zones that are outside of the healthy building range for temperature, one zone that is outside of the healthy building range for humidity, three zones that are outside of the healthy building range for carbon monoxide and one zone that is outside of the healthy building range for outside air flow. Conversely, all reporting zones are within the healthy building range for carbon dioxide and for TVOC concentration.

The illustrative dashboard 82 includes a SECURITY panel 116 that indicates for each of a number of healthy building security parameters (or KPIs), whether the current values for these parameters within any of the zones are in range or out of range, along with the number of zones that are currently in violation of healthy building guidelines. The SECURITY panel 116 includes a thermal temperature section 118, a mask compliance section 120, an intrusion detection section 122, a social distancing section 124 and an occupancy section 126. As can be seen, there are currently no incidents reported for any of thermal temperature (meaning nobody has a detected body temperature in excess of a threshold), mask compliance (meaning all detected people are complying with mask guidelines, intrusion detection and social distancing (meaning all detected people are complying with interpersonal spacing guidelines). There is one zone that appears to be violating the occupancy guidelines, likely meaning that too many people are in a particular space or zone. This could also indicate a sensor problem, if for example, people are accurately detected entering the particular space or zone, but the people leaving the particular space or zone are not accurately detected leaving. This could result in a false positive.

The illustrative dashboard 82 includes an ALARMS detail section 128, that displays additional details regarding each of the alarms that were referenced in the HEALTHY BUILDING ALARMS panel 94. If there are more current alarms then there are available lines of text within the ALARMS detail section 128, a user is able to scroll up and down through the listed alarms. In some cases, alarms with a relatively higher priority may be listed at the top of the list, and alarms with a relatively lower priority may be listed at the bottom of the list.

It is contemplated that the illustrative dashboard 82 may collect and display only parameters that have a corresponding healthy building range specified by the healthy building guidelines, but this is not required. In some cases, all available parameters that have a corresponding healthy building range specified by the healthy building guidelines are displayed in the dashboard 82. When so provided, a user may navigate to this dashboard 82 to get a good overall view of building compliance with the relevant healthy building guidelines.

Figure 5:
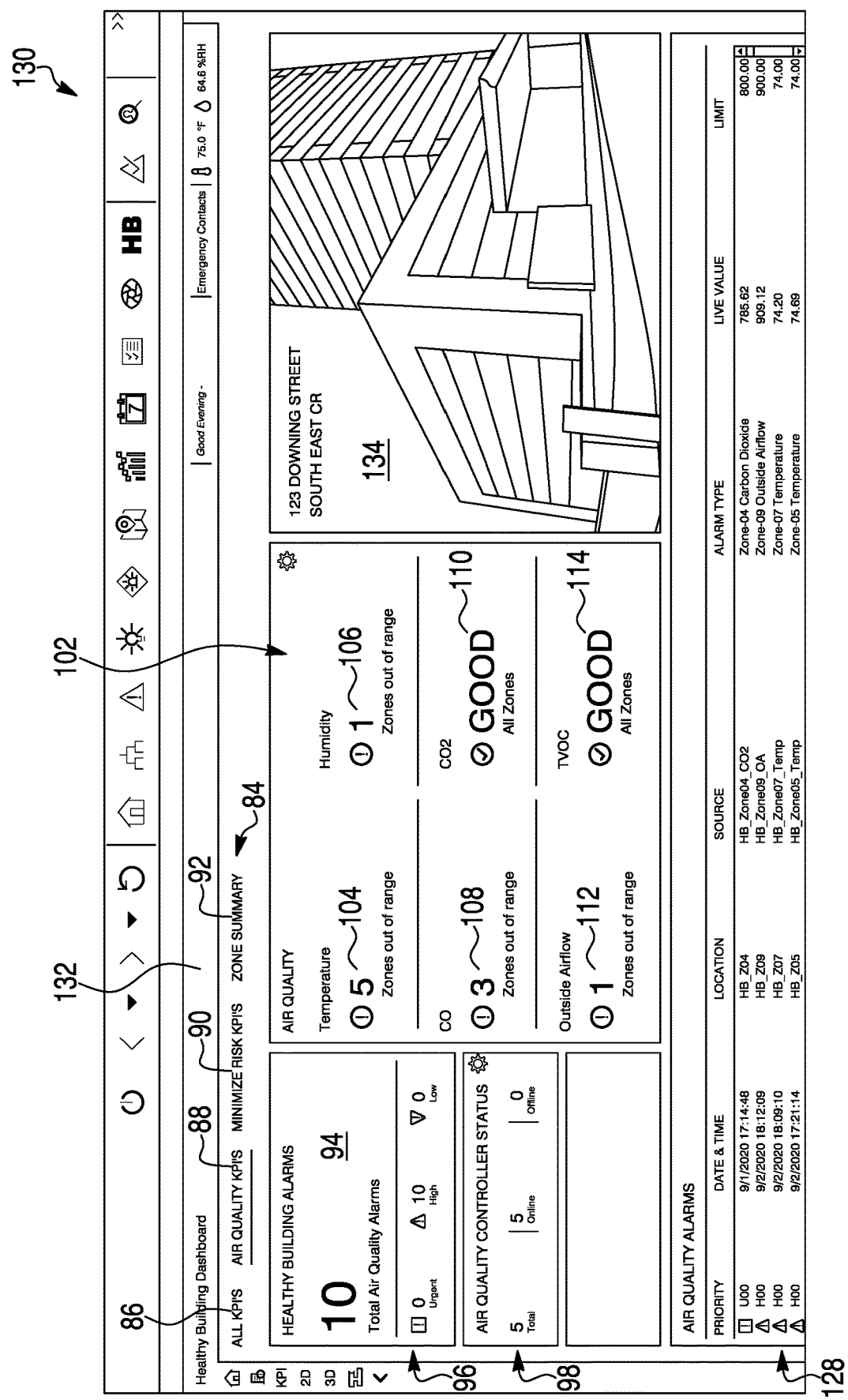

FIG. 5 shows a screen 130 that includes a dashboard 132. As can be seen from the header 84, the icon 88 for AIR QUALITY KPIS is underlined or otherwise highlighted, indicating that it has been selected. The dashboard 132 is similar to the dashboard 82, but does not display any information regarding security. Indeed, the SECURITY panel 116 shown in FIG. 4 has been replaced with a picture 134 of the building 12. This is merely representative, as any desired picture or other information can be displayed instead. In some cases, no picture 134 is displayed, and the remaining portions of the dashboard 132 are simply enlarged to fill up the available space. It should be noted that the HEALTHY BUILDING ALARMS panel 94 still includes the AIR QUALITY CONTROLLER STATUS section 98 that identifies how many air quality controllers are present and online but no longer includes the SECURITY CON- TROLLER STATUS section 100 that identifies how many security controllers are present and online.

In comparing FIG. 5 to FIG. 4, it can be seen that summary section 96 that illustrates a current number of urgent alarms, a current number of high priority alarms and a current number of low priority alarms indicates a total of 11 alarms in FIG. 4 but only indicates a total of 10 alarms in FIG. 5. This is an indication that of the 11 alarms shown in total in FIG. 4, a total of 10 alarms are air quality related while only 1 alarm is security related.

Figure 6:
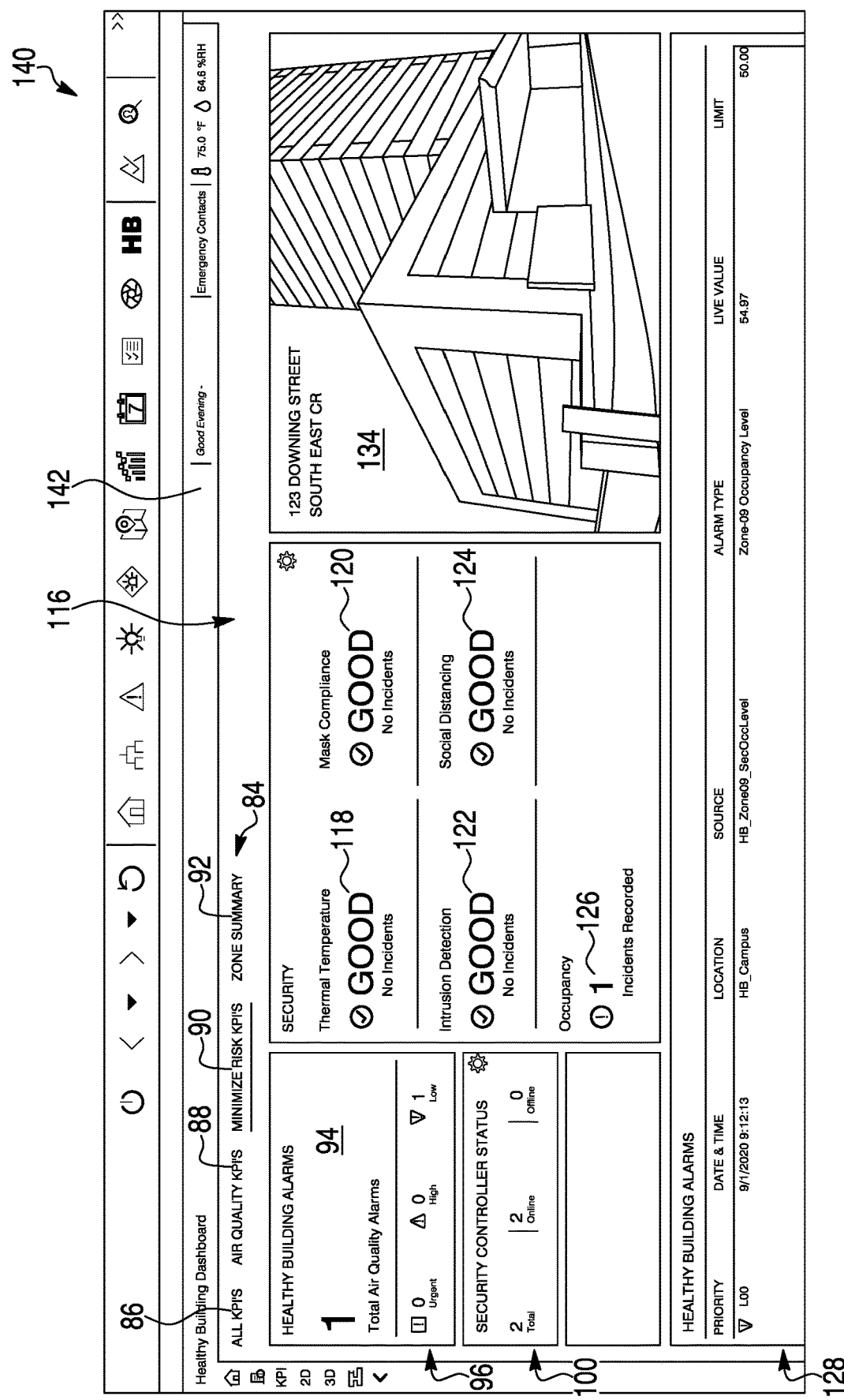

This can be seen in FIG. 6, which shows a screen 140 that includes a dashboard 142. As can be seen from the header 84, the icon 90 for MINIMIZE RISK KPIS is underlined or otherwise highlighted, indicating that it has been selected. In the summary section 96, it can be seen that there is only 1 alarm indicated. The HEALTHY BUILDING ALARMS panel 94 includes the SECURITY CONTROLLER STATUS section 100 that identifies how many security controllers are present and online, but does not include the AIR QUALITY CONTROLLER STATUS section 98 that identifies how many air quality controllers are present and online. The ALARMS detail section 128 can be seen as only including one alarm, which appears to be related to a detected occupancy level that has exceeded the healthy building range for that parameter.

FIG. 7 shows a screen 150 that includes a dashboard 152. As can be seen from the header 84, the icon 92 for ZONE SUMMARY is underlined or otherwise highlighted, indicating that it has been selected. The dashboard 152 provides greater detail into the alarms that were illustrated in FIGS. 3 through 6. The dashboard 152 includes a status column 154, a zone name column 156, a temperature column 158, a humidity column 160, an OA flow column 162, a CO2 column 164, a CO column 166, a TVOC column 168 and an OC column 170. The dashboard 152 also includes a row 172 that illustrates the healthy building range for each of the displayed parameters.

For each zone that is listed, the status column 154 indicates whether that particular zone is fully in compliance with all of the healthy building guidelines or if one or more of the sensed parameter values is outside of the healthy building range for that particular parameter. The status column 154 may include an icon that says OUT OF RANGE for a particular zone if one or more parameters within that zone are out of their healthy building range. The status column 154 may include an icon that says GOOD for a particular zone if all of the parameters within that zone are within their healthy building ranges. It will be appreciated that other words or phrases may also be used. In some cases, the icons within the status column 154 that indicate whether a particular zone is good, or is out of range, may also use color to provide a quick indication. For example, the icon may be red if out of range, green if within range. Again, other colors may also be employed.

In some cases, any parameter value that is out of range may be displayed in a different color, or may otherwise be highlighted or indicated. For example, parameter values that are within range may be displayed as white numbers on a black screen, while parameter values that are out of range may be displayed as red numbers on the black screen. In some cases, parameter values that are out of range may be bolded, or highlighted in a color. In some instances, as illustrated for example in FIG. 7, the parameter values that are out of range may be underlined.

Figure 8:
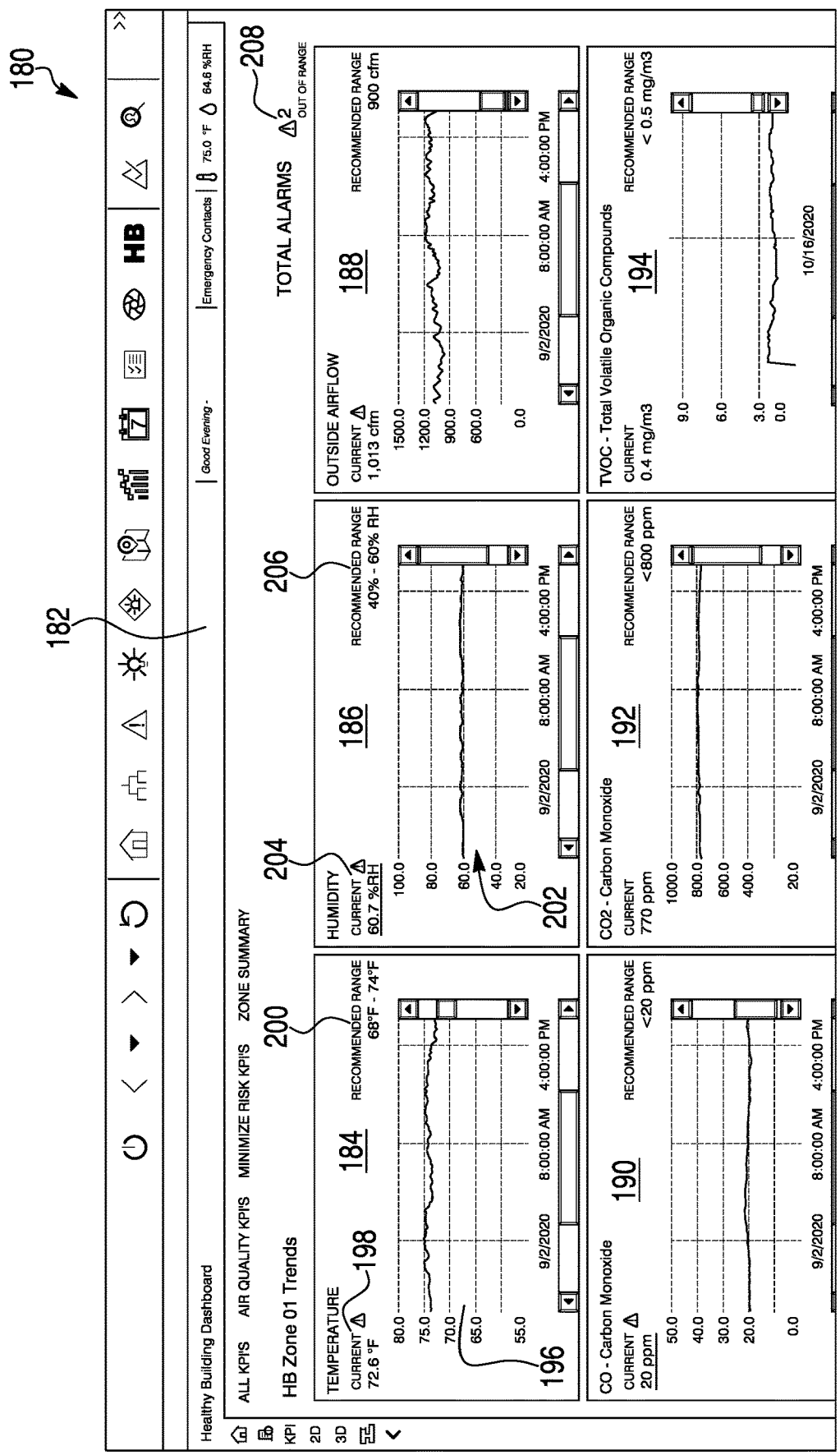

Clicking on one of the zones shown in FIG. 7 may result in additional numerical information being provided. As an example, if the "Zone 1-Reception" row 174 in FIG. 7 is selected, a screen 180 may be displayed as shown in FIG. 8. The screen 180 includes a dashboard 182. The dashboard 182 includes a graph showing trends in numerical data leading up to the currently displayed values. As shown, the dashboard 182 includes a temperature section 184, a humidity section 186, an outside airflow section 188, a CO section 190, a CO2 section 192 and a TVOC section 194. Each section displays a graph showing numerical trends for that parameter, a current measured value for that parameter and a recommended healthy building range for that parameter.

To illustrate, the temperature section 184 provides an example of a parameter value that is within range. The temperature section 184 includes a temperature graph 196 that shows how the measured temperature has been trending that day, a current temperature value 198 and a recommended range 200. As can be seen, the current temperature value of 72.6 degrees Fahrenheit is within the recommended range of 68 to 74 degrees Fahrenheit. Conversely, the humidity section 186 provides an example of a parameter value that is out of range. The humidity section 186 includes a humidity graph 202 that shows how the measured relative humidity has been trending that day, a current humidity value 204 and a recommended range 206. As can be seen, the current humidity value of 60.7 percent relative humidity exceeds the recommended range of 40 to 60 percent relative humidity.

The dashboard 182 includes an ALARMS summary 208 that shows that zone 1 has a total of 2 alarms. Looking at the dashboard 182, it can be seen that the two alarms correspond to humidity and carbon monoxide concentration. In some cases, the parameter values that are out of range may be displayed in a different color, bolded, highlighted or otherwise be displayed in a way that catches a user's attention. As illustrated, the humidity value and the carbon monoxide concentration are underlined.

FIG. 9 shows a portion of a dashboard that includes an ALARMS detail section 210 that may be considered as being an example of the ALARMS detail section 128 shown in FIGS. 4 through 6. It can be seen that the ALARMS detail section 210 includes several rows, each listing a different alarm. An operator can click on a row in order to reach a pull-down menu to provide several options, such as but not limited acknowledging the alarm. In this example, a first row 212 has been selected. The first row 212 involves a temperature value that may be out of range. In this particular example, a current temperature of 75 degrees Fahrenheit violates the healthy building range of 68 to 74 degrees Fahrenheit. Clicking on the first row 212 causes a popup menu 214 to appear. Clicking on the associated display icon 216 causes display of a screen 220, as shown in FIG. 10.

Figure 10:
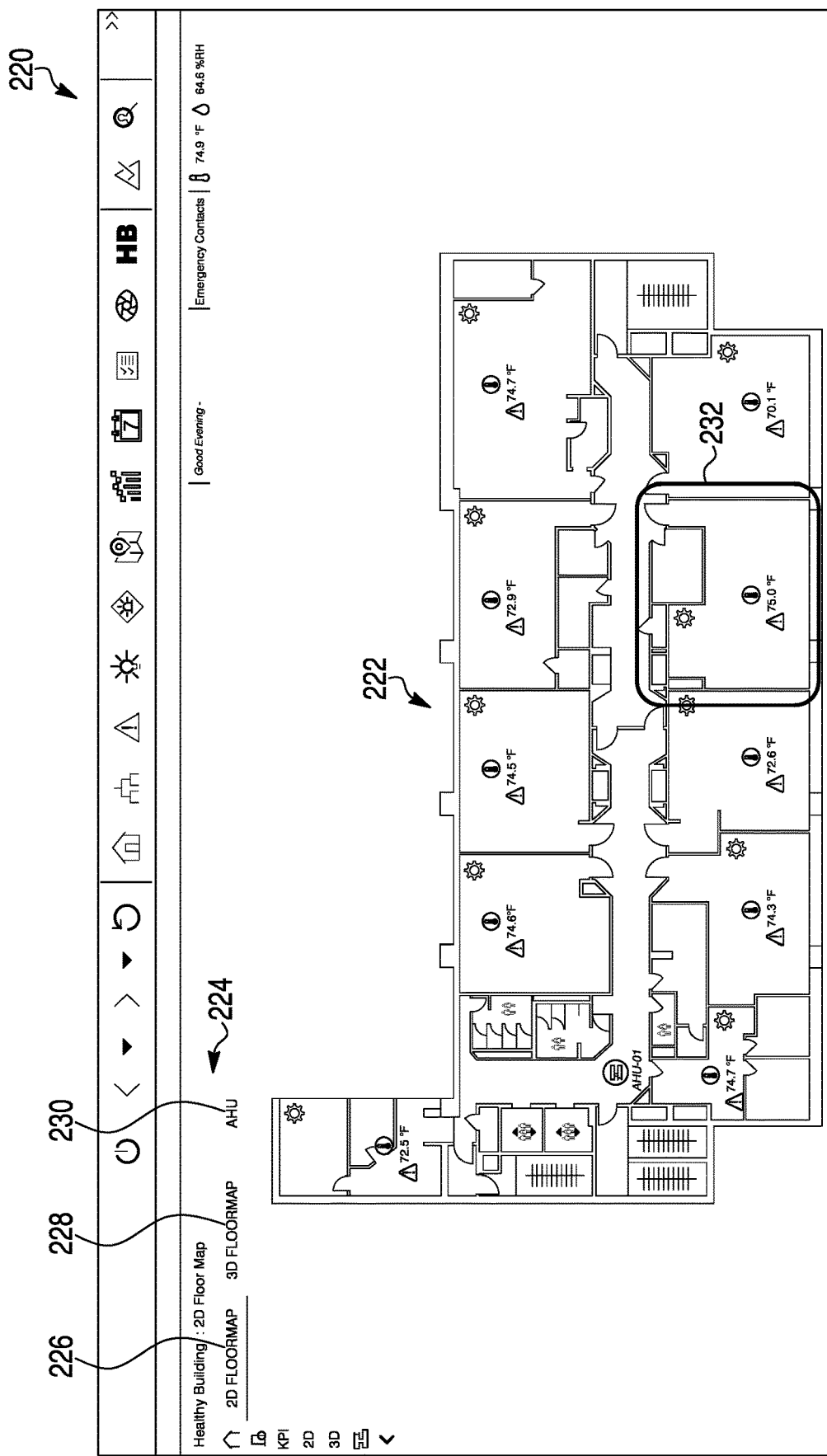

FIG. 10 shows a screen 220. The screen 220 includes a header 224 that includes an icon 226 for 2D FLOORMAP, an icon 228 for 3D FLOORMAP and an icon 230 for AHU. As can be seen, the icon 226 for 2D FLOORMAP has been selected, and accordingly the screen is displaying a two-dimensional floor plan graphic 222 that includes a number of zones. Zone 1, which is causing the temperature alarm, is indicated at 232. In some cases, any zone that has a healthy building parameter that is in the healthy building range for that parameter may be displayed in one color while any zone that has a healthy building parameter that is outside of the healthy building range for that parameter may be displayed in another color. For example, green and red may be used, respectively.

Figure 11:
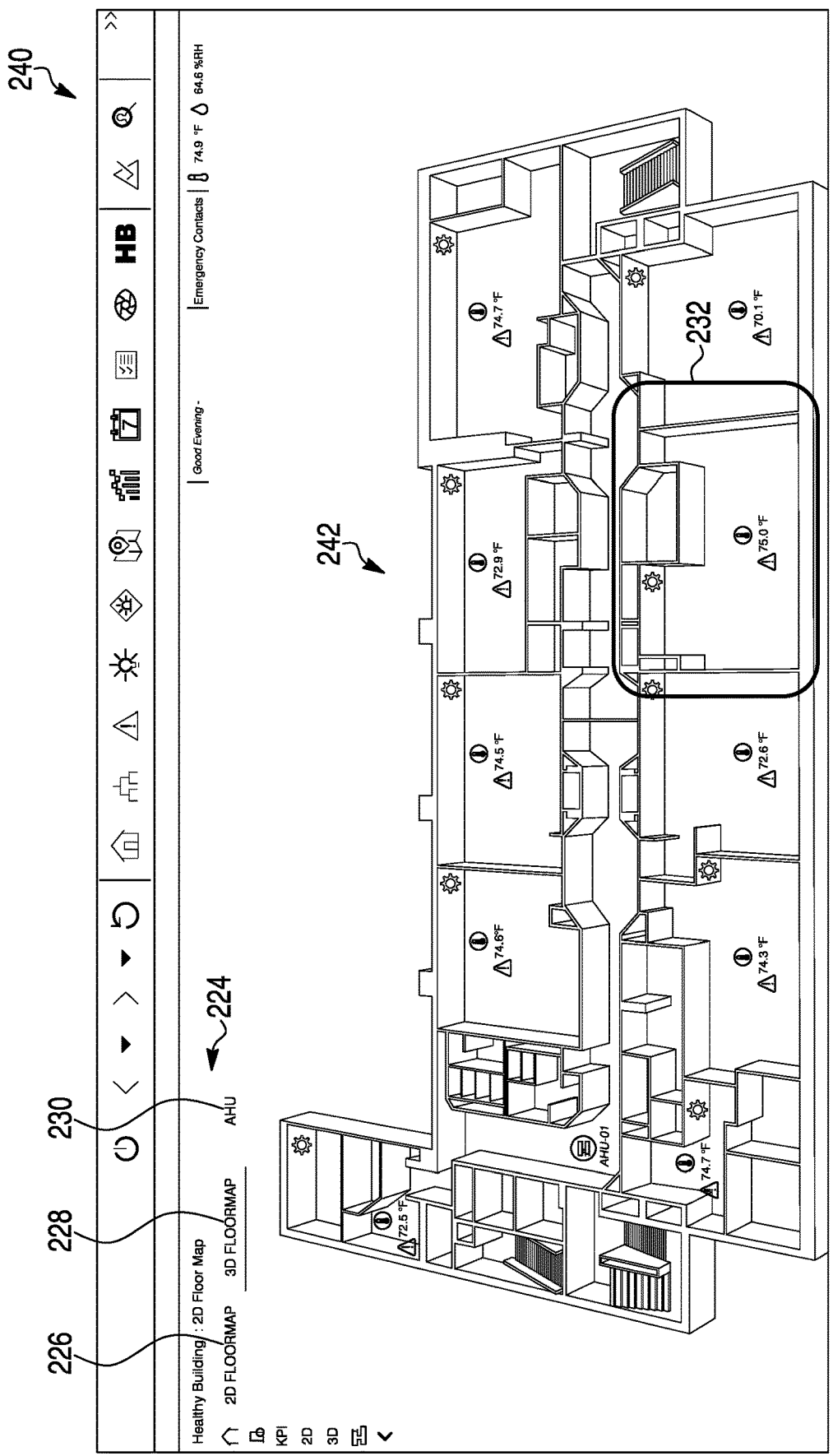

FIG. 11 shows a screen 240. As can be seen, the icon 228 for 3D FLOORMAP has been selected, and thus the screen 240 is displaying a three-dimensional floor plan graphic 242 that includes a number of zones. Zone 1, which is causing the temperature alarm, is indicated at 232. In some cases, any zone that has a healthy building parameter that is in the healthy building range for that parameter may be displayed in one color while any zone that has a healthy building parameter that is outside of the healthy building range for that parameter may be displayed in another color. For example, green and red may be used, respectively.

Figure 12:
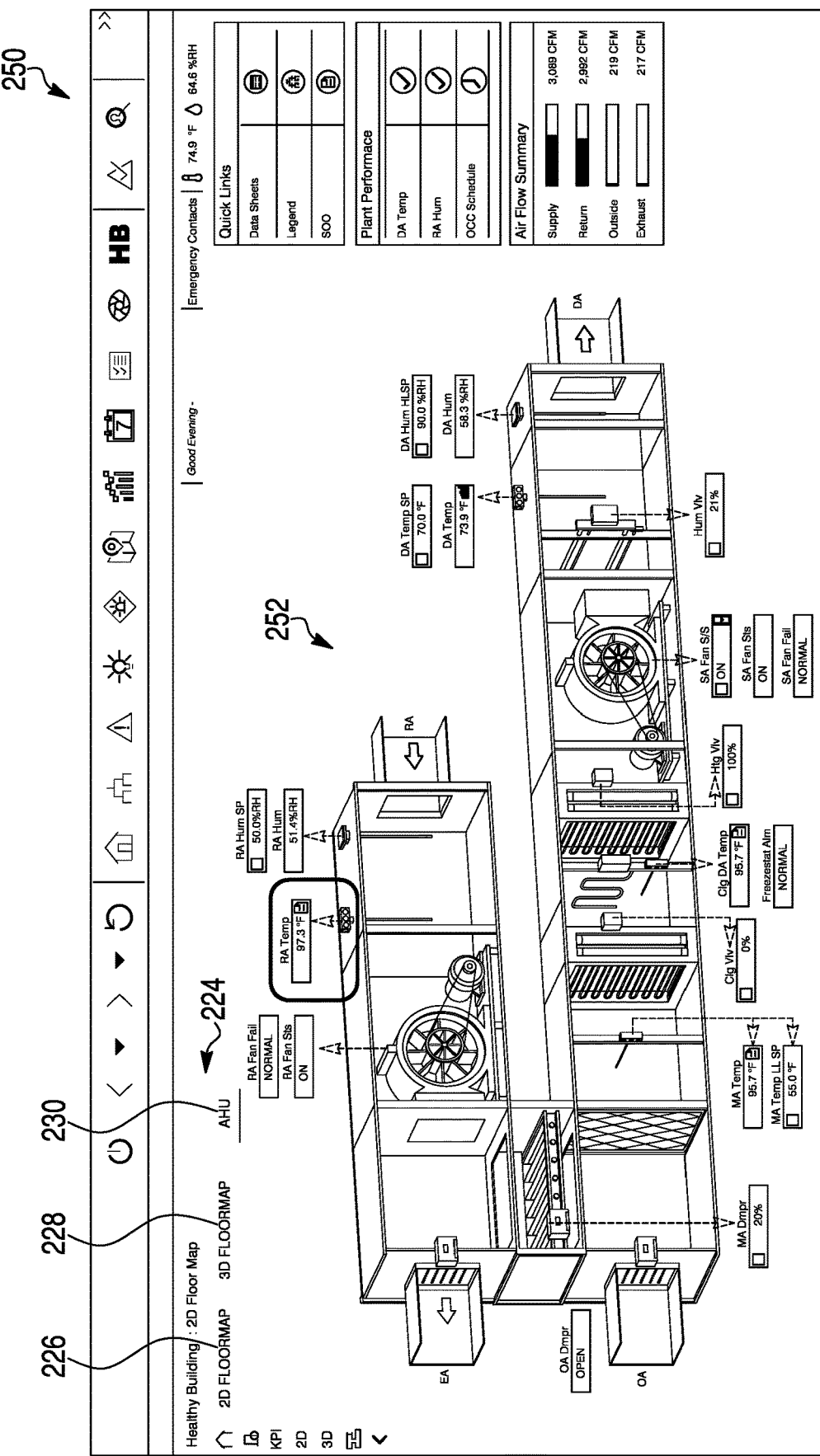

FIG. 12 shows a screen 250. As can be seen, the icon 230 for AHU has been selected, and thus the screen 250 is displaying a three dimensional graphic 252 showing the air handling equipment corresponding to the zone 1 that has a temperature value that is outside of the healthy building range. This allows a user to troubleshoot why the zone has a current temperature, or any of the other healthy building parameters, that is currently outside of the healthy building range for that particular healthy building parameter.

Figure 13:
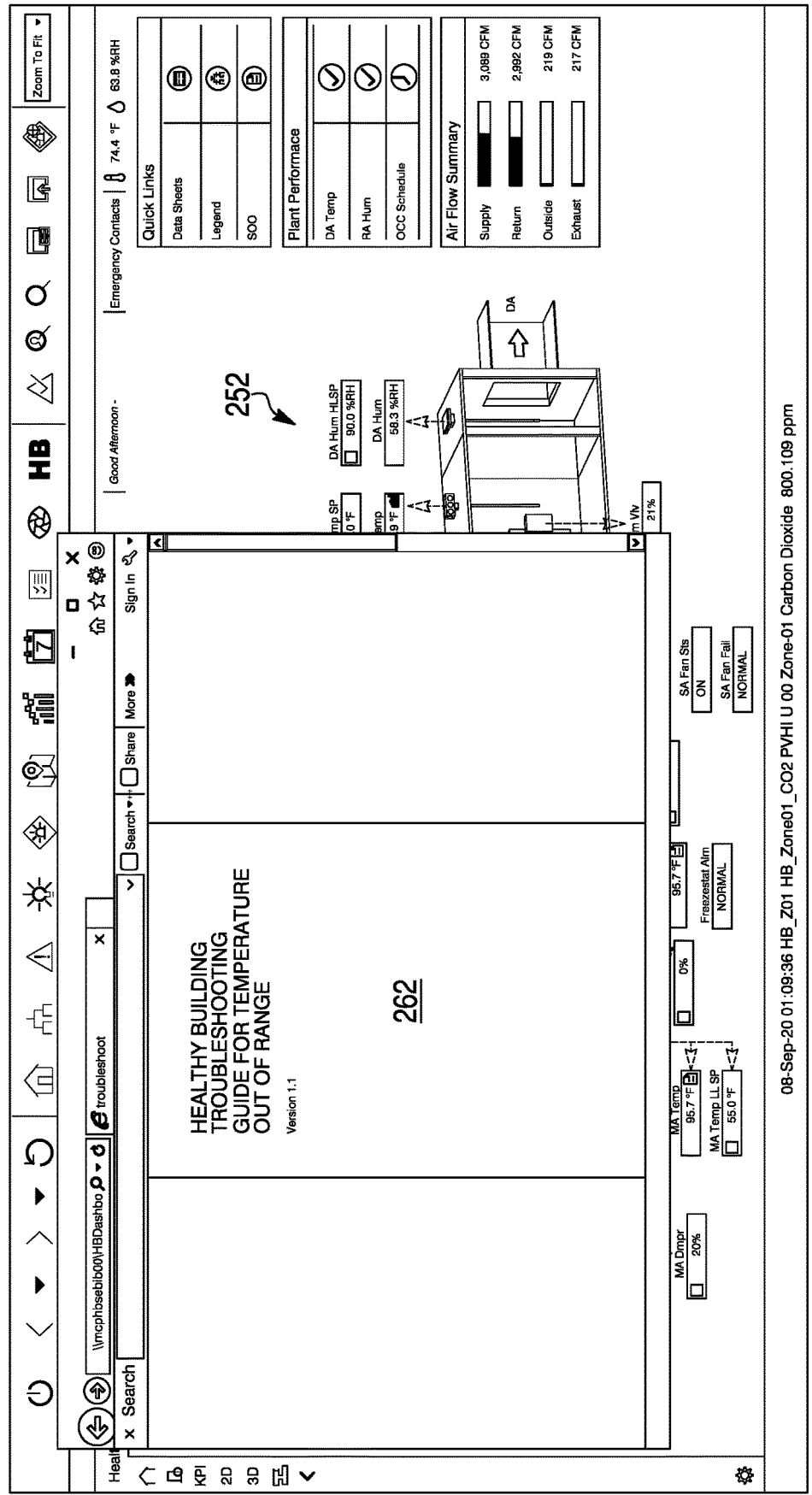

FIG. 13 shows a screen 260 that is similar to the screen 250 shown in FIG. 12, but includes a popup 262 that provides the user with additional information with how to resolve a healthy building parameter that is out of its healthy building range. As illustrated, the popup 262 includes documentation pertaining to troubleshooting a temperature that is out of range. The popup 262 may, for example, be a PDF format document that the user can scroll through. In some cases, the popup 262 may, for example, include a link to a video clip that guides the user through troubleshooting an out of range temperature value. The popup 262 may, for example, include a link to an appropriate Youtube.com link.

Figure 14:
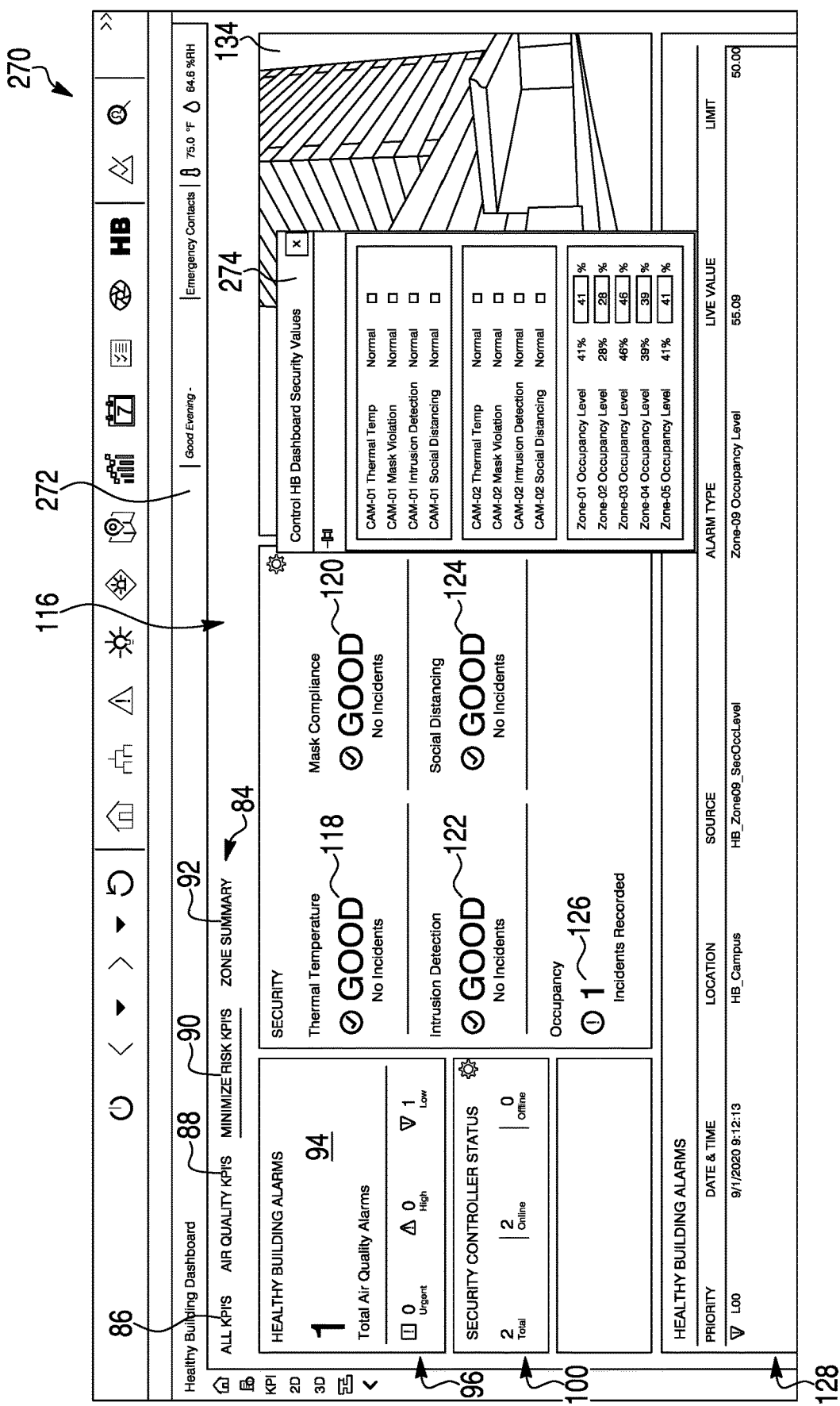

FIG. 14 shows a screen 270 that includes a dashboard 272. The dashboard 272 is similar to the dashboard 142 shown in FIG. 6, but includes a popup 274 that includes additional status data. In this particular example, the popup 274 includes details for CAM1 (Security Video Camera-1), including detected thermal temperatures, mask violation, intrusion detection and social distancing. Each of these can be determined via video analysis. The popup 274 also includes similar details for CAM2. The popup 274 also lists occupancy status for each zone.

Figure 16:
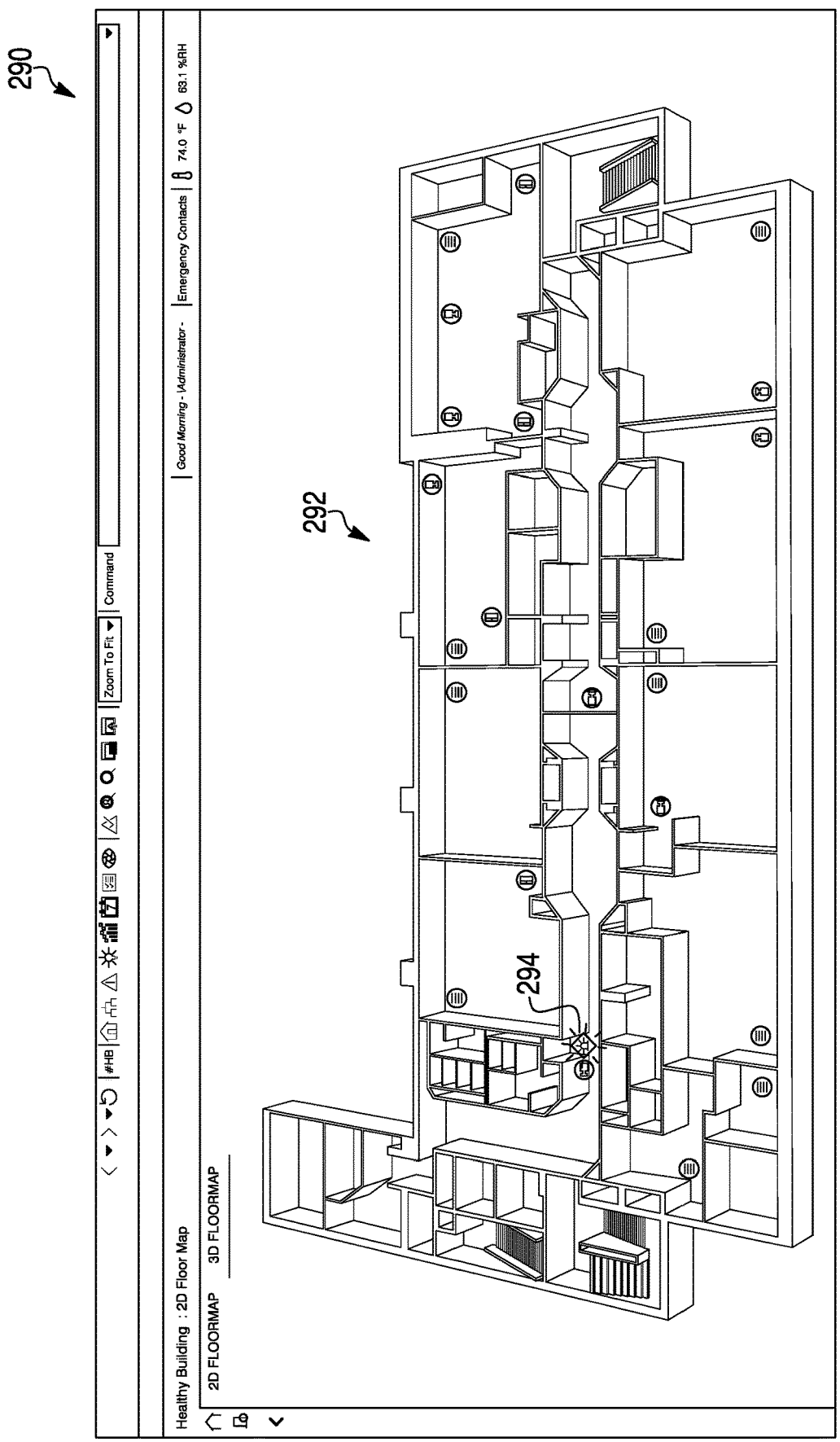

FIG. 15 shows a portion of a dashboard that includes an ALARMS detail section 280. It can be seen that the ALARMS detail section 280 includes several rows, each listing a different alarm. An operator can click on a row in order to reach a pull-down menu to provide several options, such as but not limited acknowledging the alarm. In this example, a first row 282 has been selected. The first row 282 involves a camera-indicated thermal alarm. This may indicate a person who has a camera-indicated body temperature that is high enough to trigger an alarm. Clicking on the first row 282 causes a popup menu 284 to appear. Clicking on the associated display icon 286 causes display of a screen 290, as shown in FIG. 16.

The screen 290 includes a three-dimensional floorplan graphic 292. The three-dimensional floorplan graphic 292 may include icons for cameras, doors, card readers, intercoms and the like. Clicking on a particular icon may pull up additional information. In FIG. 16, a camera icon 294 is highlighted. The camera icon 294 represents the particular camera that detected the possible thermal temperature violation. While the camera icon 294 is shown as highlighted, in some cases the camera icon 294 may be shown larger, or in a different color, than other camera icons present on the screen 290.

Figure 17:
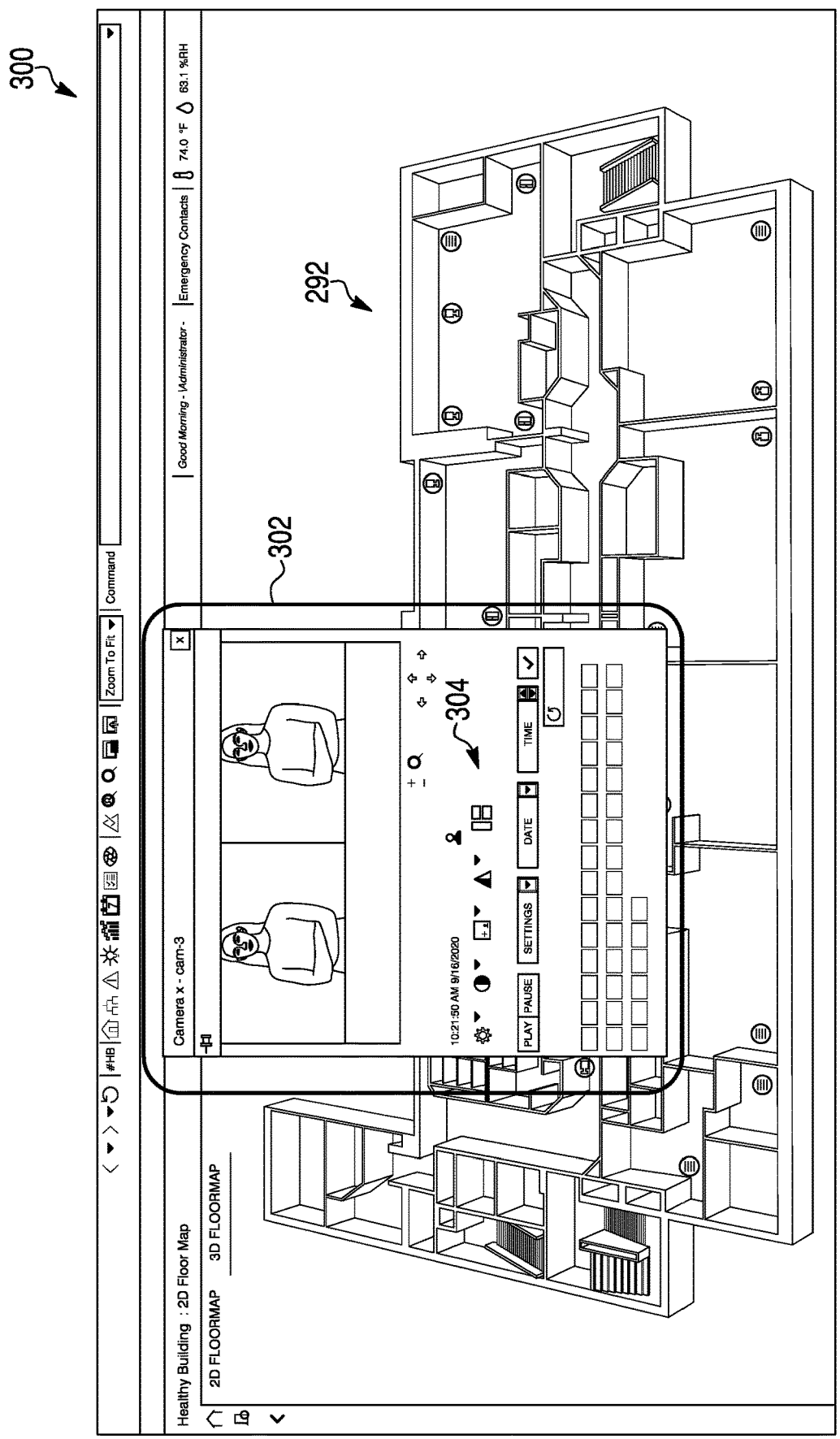

Clicking on the camera icon 294 will cause display of a screen 300, as shown in FIG. 17. The screen 300 includes a pop-up 302 that includes one or more images as captured by the camera represented by the camera icon 294. It will be appreciated that the images may be displayed in color, with different colors representing different detected skin temperatures. For example, blues may represent relatively lower temperatures while reds may represent relatively higher temperatures. This is merely illustrative, as any desired color scheme may be used. The pop-up 302 includes a set 304 of video controls, such as play, pause and the like, that a user may utilize to review video. The system may automatically identify the person in the video with the elevated skin temperature by using facial recognition or the like. In some cases, the persons contact information may be displayed in pop-up 302.

Figure 18:
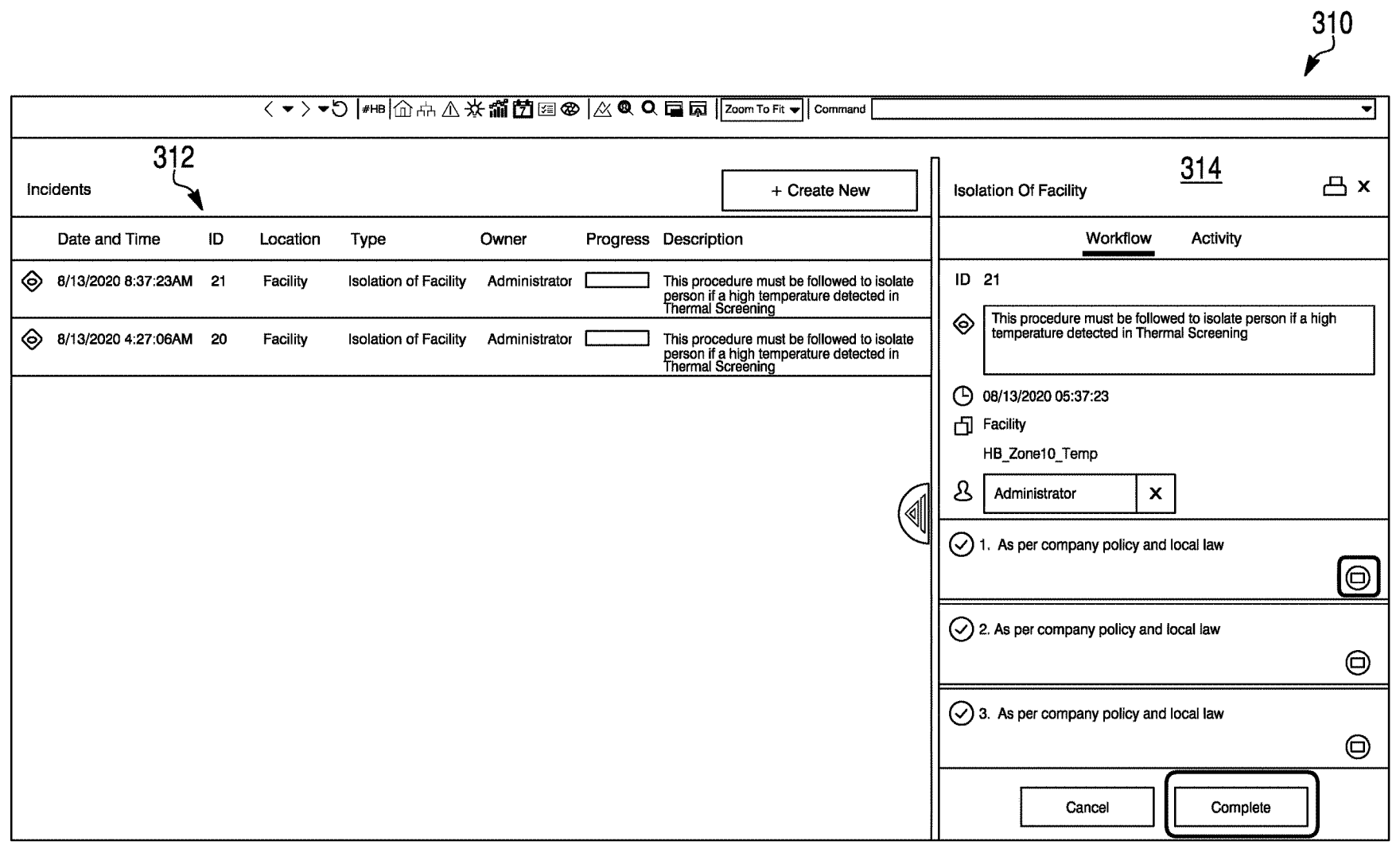
Figure 19:
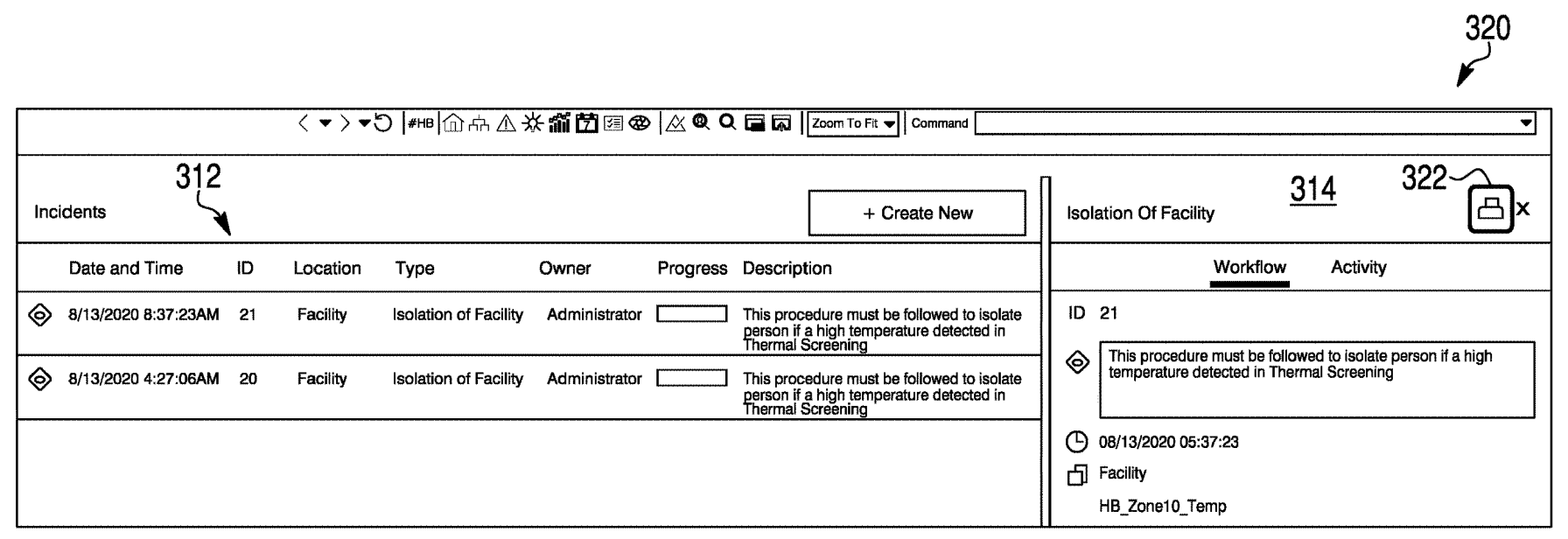

FIG. 18 shows a screen 310 that may be displayed in response to selecting an icon in FIG. 17. The screen 310 includes an Incident Workflow 312 that shows each open incident. Clicking on one of the workflows shown within the Incident Workflow 312 will open that incident on the right-side 314 of the screen 310. The Incident Workflow 312 may be a predefined Standard Operating Procedure (SOE) that defines a set of steps that the operator should take to address the corresponding incident. FIG. 19 shows a similar screen 320. Reports may be accessed by clicking a Report icon 322. While shown as a printer icon, it will be appreciated that other icons or graphics may also be used.

FIG. 20 shows a screen 330 that includes an incident report 332 that may be provided in response to the user clicking the Report icon 322 in FIG. 19. The incident report 332 may include all details including an alarm summary, incident life cycle and workflow action with operator details and date-time stamp.

Figure 21:
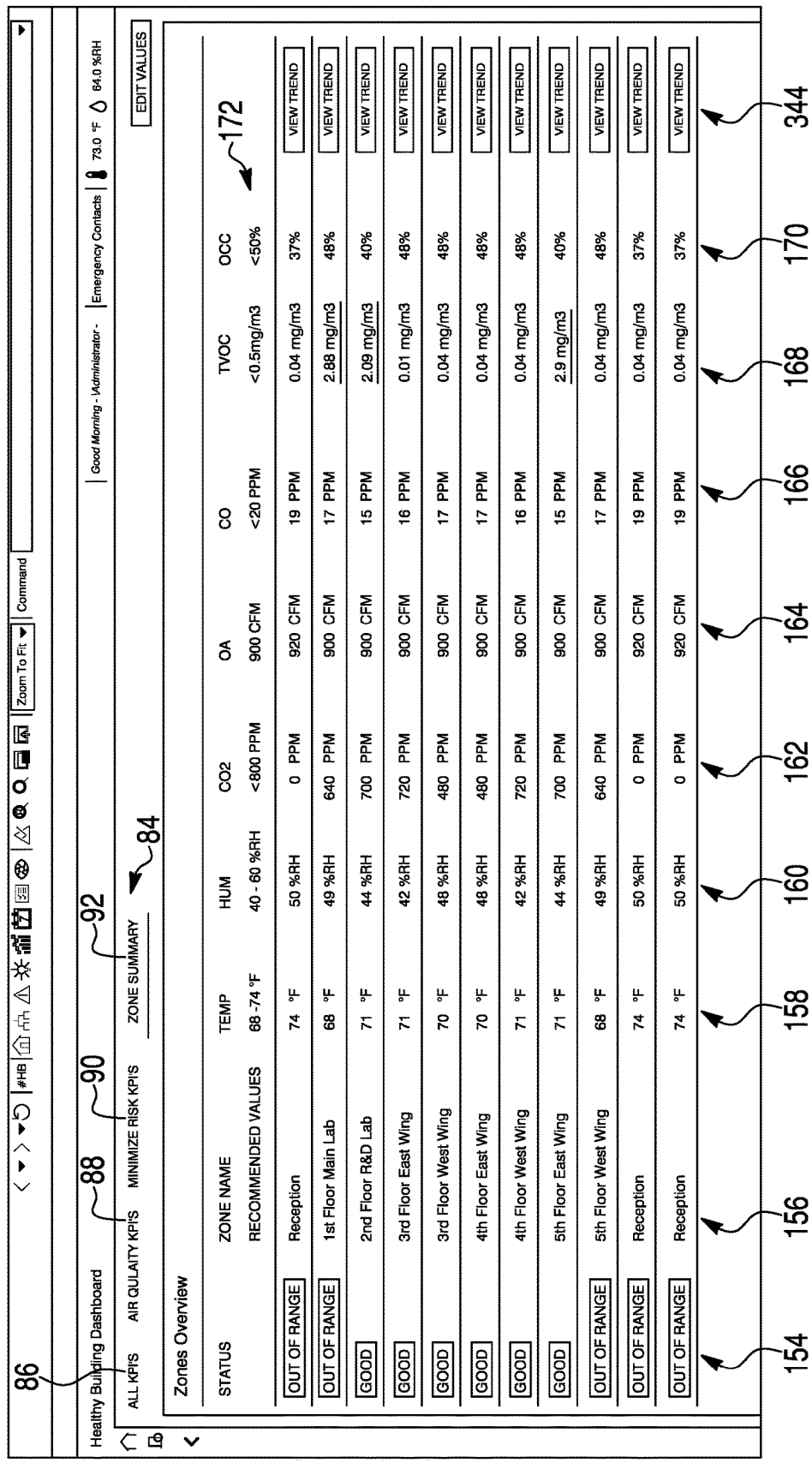

FIG. 21 shows a screen 340 that includes a dashboard 342. The dashboard 342 is similar to the dashboard 152 shown in FIG. 7, but includes a column 344 that includes for each row a VIEW TREND button. It will be appreciated that selecting the appropriate VIEW TREND button in the column 344 may cause display of a dashboard similar to the dashboard 182 shown in FIG. 8.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method of monitoring building compliance with healthy building guidelines, the healthy building guidelines specifying desired ranges for each of a plurality of different parameters, the method comprising:
  obtaining current parameter values for a plurality of different parameters from a plurality of sensors disposed within a plurality of different zones of a building;
  for each parameter:
    comparing each current parameter value received from each of the plurality of different zones with a corresponding healthy building range for that parameter as specified by the healthy building guidelines; and
    displaying a healthy building dashboard including one or more screens that includes a summary showing for each of the plurality of different parameters:
      how many zones of the plurality of different zones of the building are within the corresponding healthy building range for that parameter and/or how many zones of the plurality of different zones are not within the corresponding healthy building range for that parameter; and
  modifying operation of one or more building system components in order to drive a parameter that is outside of its corresponding healthy building range towards a value that is within its corresponding healthy building range.

2. The method of claim 1, further comprising displaying one or more windows that instruct a user how to correct for a parameter that is outside of its corresponding healthy building range.

3. The method of claim 1, wherein the healthy building dashboard further includes a summary of healthy building alarms, wherein each health building alarm corresponds to a parameter in a zone not falling within its corresponding healthy building range.

4. The method of claim 1, wherein one of the plurality of different parameters corresponds to air temperature, and its corresponding healthy building range is 68 and 74 degrees Fahrenheit as specified in the healthy building guidelines to help reduce the spread of disease in the building.

5. The method of claim 1, wherein one of the plurality of different parameters corresponds to relative humidity, and its corresponding healthy building range is 40 and 60 percent as specified in the healthy building guidelines to help reduce the spread of disease in the building.

6. The method of claim 1, wherein one of the plurality of different parameters corresponds to carbon dioxide concentration, and its corresponding healthy building range is less than 800 parts per million (ppm) as specified in the healthy building guidelines to help reduce the spread of disease in the building.

7. The method of claim 1, wherein one of the healthy building ranges comprises one of:
    a carbon monoxide concentration of less than 20 ppm;
    a total volatile organic compound (TVOC) concentration of less than 0.5 mg/m$^3$; and
    an occupancy percentage of less than 50 percent of a specified maximum occupancy.

8. The method of claim 1, wherein the healthy building dashboard includes a summary of healthy building security parameters, wherein the healthy building security parameters include one or more of:
    an occupant temperature compliance parameter that relates to a status of occupant temperature compliance of occupants of the building;
    a mask compliance parameter that relates to a status of mask compliance of occupants of the building with one or more mask guidelines specified by the healthy building guidelines;
    a social distancing compliance parameter that relates to a status of social distancing compliance of occupants of the building with one or more social distancing guidelines specified by the healthy building guidelines; and
    a maximum occupancy compliance parameter that relates to a status of maximum occupancy compliance of occupants of the building with one or more maximum occupancy guidelines specified by the healthy building guidelines.

9. The method of claim 1, wherein the healthy building dashboard includes a zone summary that for each of the plurality of different zones, displays each current parameter value measured within that zone.

10. The method of claim 9, wherein the zone summary highlights any current parameter value in any zone of the plurality of different zones that is currently outside of the healthy building range for that parameter.

11. The method of claim 9, wherein the zone summary includes a recitation of the corresponding healthy building range for each of the parameters.

12. The method of claim 9, wherein the zone summary includes links that when selected by a user, additional information is displayed.

13. The method of claim 12, wherein the additional information includes numerical values for one or more of the plurality of different parameters displayed over time to show trends.

14. A method of monitoring compliance with healthy building guidelines, the healthy building guidelines specifying desired ranges for each of a plurality of different sensed parameters, the method comprising:
    receiving parameter values for a plurality of different sensed parameters in a building;
    comparing current values for each of the plurality of different sensed parameters to a corresponding healthy building range specified in the healthy building guidelines to help reduce the spread of disease in the building;
    displaying a healthy building dashboard on a display that indicates for each of the plurality of different sensed parameters whether any areas of the building are not within the healthy building range for that sensed parameter;
    controlling one or more building system components within the building to drive current values for one or more of the sensed parameters that are outside of the corresponding healthy building range towards a value within the corresponding healthy building range; and
    in response to a user request, displaying on the display additional information pertaining to the areas of the building for which one or more of the sensed parameters are outside of the healthy building range for that sensed parameter.

15. The method of claim 14, further comprising controlling one or more building system components within the building to drive current values for one or more of the sensed parameters that are outside of the corresponding healthy building range to a predefined setpoint that is within the corresponding healthy building range.

16. A non-transient, computer-readable storage medium storing instructions that when executed by a processor cause the processor to:
    receive parameter values for a plurality of different sensed parameters in a building over time;
    compare current values for each of the plurality of different sensed parameters to a healthy building range specified for each of the plurality of different sensed parameters;
    display a dashboard on a display that indicates for each of the plurality of different sensed parameters whether any areas of the building are not within the healthy building range for that sensed parameter;
    control one or more building system components within the building to drive current values for one or more of the sensed parameters that are outside of the healthy building range for that sensed parameter towards a value within the healthy building range for that sensed parameter; and
    in response to a user request, display on the display additional information pertaining to the areas of the building for which one or more of the sensed parameters are outside of the healthy building range for that sensed parameter.

17. The non-transient, computer-readable storage medium of claim 16, wherein the plurality of different sensed parameters corresponds to one or more of:

air temperature, wherein the corresponding healthy building range is 68 and 74 degrees Fahrenheit to help reduce the spread of disease in the building; and relative humidity, wherein the corresponding healthy building range is 40 and 60 percent to help reduce the spread of disease in the building.

* * * * *